(12) United States Patent
Kotanko et al.

(10) Patent No.: US 10,203,321 B2
(45) Date of Patent: *Feb. 12, 2019

(54) METHOD OF IDENTIFYING WHEN A PATIENT UNDERGOING HEMODIALYSIS IS AT INCREASED RISK OF DEATH

(75) Inventors: Peter Kotanko, New York, NY (US); Stephan Thijssen, New York, NY (US); Len Usvyat, Philadelphia, PA (US); Nathan W. Levin, New York, NY (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 533 days.

This patent is subject to a terminal disclaimer.

(21) Appl. No.: 13/989,370

(22) PCT Filed: Dec. 1, 2011

(86) PCT No.: PCT/US2011/062774
§ 371 (c)(1),
(2), (4) Date: May 23, 2013

(87) PCT Pub. No.: WO2012/075222
PCT Pub. Date: Jun. 7, 2012

(65) Prior Publication Data
US 2013/0244263 A1    Sep. 19, 2013

Related U.S. Application Data

(60) Provisional application No. 61/419,089, filed on Dec. 2, 2010.

(51) Int. Cl.
*G01N 33/50* (2006.01)
*G06F 19/00* (2018.01)
*G01N 33/68* (2006.01)

(52) U.S. Cl.
CPC ..... *G01N 33/5091* (2013.01); *G01N 33/6893* (2013.01); *G06F 19/00* (2013.01); *G01N 2800/347* (2013.01); *G01N 2800/56* (2013.01); *Y10T 436/147777* (2015.01); *Y10T 436/166666* (2015.01)

(58) Field of Classification Search
CPC ... G06F 19/3431; A61B 5/00; G01N 2800/50; G01N 2800/52; G01N 2800/56; G01N 2800/347; G01N 33/5091; G01N 33/6893; Y10T 436/166666
See application file for complete search history.

(56) References Cited

U.S. PATENT DOCUMENTS

| 4,957,115 A | 9/1990 | Selker |
| 6,059,724 A | 5/2000 | Campell et al. |
| 6,454,707 B1 | 9/2002 | Casscells et al. |
| 6,645,153 B2 | 11/2003 | Kroll et al. |
| 9,883,799 B2 | 2/2018 | Kotanko et al. |
| 2003/0083901 A1 | 5/2003 | Bosch et al. |
| 2003/0092975 A1 | 5/2003 | Casscells et al. |

(Continued)

FOREIGN PATENT DOCUMENTS

| JP | 2007/000238 A | 1/2007 |
| WO | WO 2011/133869 A1 | 10/2011 |
| WO | WO 2012/075222 A2 | 6/2012 |

OTHER PUBLICATIONS

Beto, JA; Bansal, VK; Ing, TS; Daugirdas JT "Variation in blood sample collection for determination of hemodialysis adequacy. Council on Renal Nutrition National Research Question Collaborative Study Group" Am J Kidney Dis. Jan. 1998, 31(1), pp. 135-141 (abstract only) doi:10.1053/ajkd.1998.v31.pm9428465.*

AnabolicMinds.com "Halodrol/H-Drol is Suppressive . . . My Scanned Blood Work Inside", <URL: http://anabolicminds.com/forum/steroids/71773-halodrol-h-drol.html> Jul. 7, 2007, accessed online Jul. 12, 2105, 4 pages.*

Renal Dialysis Center of the Ohio State University Medical Center "Blood Tests for Dialysis" The Ohio State University, <archived online URL:https://patienteducation.osumc.edu/Documents/bloodtst.pdf>, Sep. 1, 2010, 4 pages.*

(Continued)

*Primary Examiner* — Aaron J Kosar
(74) *Attorney, Agent, or Firm* — Hamilton, Brook, Smith & Reynolds, P.C.

(57) ABSTRACT

The invention is directed to a method of identifying a patient undergoing periodic hemodialysis treatments at increased risk for death that includes determining at least one of the patient's clinical or biochemical parameters, consisting of serum bicarbonate concentration level, serum potassium concentration level, serum calcium concentration level, hemoglobin concentration level, serum phosphorus concentration level, neutrophil to lymphocyte ratio, equilibrated normalized protein catabolic rate (enPCR), equilibrated fractional clearance of total body water by dialysis and residual kidney function (eKdrt/V), EPO resistance index, transferrin saturation index, serum ferritin concentration level, serum creatinine concentration level, platelet count, Aspartat-Aminotransferase level, and Alanin-Aminotransferase level at periodic hemodialysis treatments, and identifying a patient as having an increased risk for death if the patient has a significant change in the rate of change of at least one of the patient's clinical or biochemical parameters. The invention is also directed to a method of identifying an increased mortality risk factor for a patient undergoing periodic hemodialysis treatment. The method includes analyzing data of deceased patients that were previously undergoing periodic hemodialysis treatments by performing a longitudinal analysis backwards in time of changes in a clinical or biochemical parameter the patients, and identifying a significant change in the rate of decline or the rate of increase in a clinical or biochemical parameter before death of the patients.

9 Claims, 19 Drawing Sheets

(56) References Cited

U.S. PATENT DOCUMENTS

| | | |
|---|---|---|
| 2004/0260185 A1 | 12/2004 | Anderson et al. |
| 2005/0137481 A1 | 6/2005 | Sheard |
| 2006/0226079 A1 | 10/2006 | Mori |
| 2007/0179815 A1 | 8/2007 | Vining et al. |
| 2007/0244724 A1 | 10/2007 | Pendergast et al. |
| 2007/0248981 A1 | 10/2007 | Snider et al. |
| 2008/0076187 A1 | 3/2008 | Chen |
| 2009/0030862 A1 | 1/2009 | King et al. |
| 2009/0076345 A1 | 3/2009 | Manicka et al. |
| 2009/0082684 A1 | 3/2009 | Sornmo |
| 2009/0265190 A1 | 10/2009 | Ashley et al. |
| 2010/0057490 A1 | 3/2010 | Kocis et al. |
| 2010/0099958 A1 | 4/2010 | Kotanko et al. |
| 2010/0151463 A1 | 6/2010 | Baehner et al. |
| 2010/0273207 A1 | 10/2010 | Langley et al. |
| 2011/0137136 A1* | 6/2011 | Kotanko .................. A61B 5/00 600/301 |
| 2013/0041684 A1* | 2/2013 | Kotanko ................ G16H 50/70 705/2 |

OTHER PUBLICATIONS

International Preliminary Report on Patentability for PCT/US2011/062774 dated Feb. 24, 2014 entitled "Method of Identifying When a Patient Undergoing Hemodialysis Is At Increased Risk of Death", 5 pages.

Goldwasser, P., et al., "Predictors of Mortality in Hemodialysis Patients," J. Am. Soc. Nephrol. 3: 1613-1622 (Mar. 1993).

Li, Z., et al., "The Epidemiology of Systolic Blood Pressure and Death Risk in Hemodialysis Patients," Am. J. Kidney Dis. 48(4): 606-615 (Oct. 2006).

Notification of Transmittal of the International Search Report and the Written Opinion of the International Searching Authority for Int'l Application No. PCT/US2011/062774; "Method of Identifying When a Patient Undergoing Hemodialysis Is At Increased Risk of Death," 13 pages, dated Apr. 9, 2012.

Abbott, R.D., "Logistic Regression in Survival Analysis", American Journal of epidemiology, 121(3): 465-471 (1985).

Annesi, I., et al., "Efficiency of the Logistic Regression and Cox Proportional Hazards Models in Longitudinal Studies", Statistics in Medicine, 8:1515-1521 (1989).

Balon, B.P., et al., "Fetuin-A As a Risk Factor for Mortality in Hemodialysis", Wien Klin Wochenschr, 122(Supp. 2): 63-67 (2010).

Caravaca, F., et al., "Predictores de la Mortalidad Precoz en Diálisis", Nefrologia, XXI: 274-282 (2001) With English Summary.

Chertow, G.M., et al., "Predictors of Mortality and the Provisions of Dialysis in Patients with Acute Tubular Necrosis", Journal of the American Society of Nephrology, 9:692-698 (1998).

Chertow, G.M., et al., "Mortality After Acute Renal Failure: Models for Prognostic Stratification and Risk Adjustment", Kidney International, 70:1120-1125 (2006).

Daugirdas, J.T., Handbook of Dialisys, A Lippincott Williams & Wilkins Handbook, pp. 462-605 (2007).

G.M. Fitmaurice, et al., "Modelling the Covariance." In Applied Longitudinal Analysis, Wiley Series in Probability and Statistics, (2004).

Gilbertson, D.T., et al., "Hemoglobin Level Variability: Associations With Mortaltiy", Clin J Am Soc Nephrol 3: 133-138 (2008).

Kleinbaum, D.G. and Klein, M., "Logistic Regression". In Statistics for Biology and Health, 2nd Ed., pp. 1-8 (2005).

Kontanko, P., et al., "Temporal Evolution of Clinical Parameters Before Death in Dialysis Patients: A New Concept", Blood Purification, 27: 38-47 (2009).

Kovedsy, C.P., et al., "Serum and Dialysate Potassium Concentrations and Survival in Hemodialysis Patients", Clin J Am Soc Nephrol, 2: 999-1007 (2007).

Regidor, D.L., et al., Associations Between Changes in Hemoglobin and Administered Erythropoiesis-Stimulating Agent and Survival in Hemodialysis Patients, J Am Soc Nephrol 17: 1181-1191 (2006).

Stosovic, M., et al., "Nerve Conduction Studies and Prediction of Mortality in Hemodialysis Patients", Renal Failure, 30:695-699 (2008).

Wu, D.Y., et al., "Associateion Between Serum Bicarbonate and Death in Hemodialysis Patients: Is It Better to Acidotic or Alkalotic?", Clin J Am Soc Nephrol, 1: 70-78 (2006).

Supplementary Partial European Search Report for EP application No. 11845234, "Method of Identifying When a Patient Undergoing Hemodialysis Is At Increased Risk of Death", dated Apr. 29, 2015.

Notification of Transmittal of the International Search Report and the Written Opinion of the International Searching Authority for PCT/US2011/033590, "System and Method of Identifying When a Patient Undergoing Hemodialysis Is At Increased Risk of Death by a Logistic Regression Model", dated Jul. 22, 2011.

International Preliminary Report on Patentabiligy for PCT/US2011/033590, "System and Method of Identifying When a Patient Undergoing Hemodialysis Is At Increased Risk of Death by a Logistic Regression Model", dated Nov. 1, 2012.

Extended European Search Report for EP application No. 11845234, "Method of Identifying When a Patient Undergoing Hemodialysis Is At Increased Risk of Death", dated Aug. 14, 2015.

Duman, S., et al., "Post-Dialysis Potassium and Pre-Dialysis Socium Levels as Predictors of Death in Hemodialysis Patients", Nephrology Dialysis Transplantation, 22(Supp1.6): p. 193 (2007).

Ruppert, D., et al., "Semiparametric Regression". In Cambridge Series in Statistical and Probabilistic Mathematics, Cambridge University Press: pp. 57-111 (2003).

Examiner's Answer to Appeal Brief filed Jan. 9, 2015 for U.S. Appl. No. 12/959,017, "Method of Identifying When a Patient Undergoing Hemodialysis Is At Increased Risk of Death", dated May 7, 2015.

Final Office Action for U.S. Appl. No. 12/959,017, "Method of Identifying When a Patient Undergoing Hemodialysis Is At Increased Risk of Death", dated Jul. 10, 2014.

Final Office Action for U.S. Appl. No. 12/959,017, "Method of Identifying When a Patient Undergoing Hemodialysis Is At Increased Risk of Death", dated Sep. 19, 2012.

Final Office Action for U.S. Appl. No. 13/642,364, System and Method of Identifying When a Patient Undergoing Hemodialysis Is At Increased Risk of Death by a Logistic Regression Model, dated Feb. 11, 2016.

Interview Summary for U.S. Appl. No. 12/959,017, "Method of Identifying When a Patient Undergoing Hemodialysis Is At Increased Risk of Death", dated Mar. 21, 2014.

Non-final Office Action for U.S. Appl. No. 12/587,941, "Method of Identifying When a Patient Undergoing Hemodialysis Is At Increased Risk of Death", dated Mar. 5, 2012.

Non-final Office Action for U.S. Appl. No. 12/959,017, "Method of Identifying When a Patient Undergoing Hemodialysis Is At Increased Risk of Death", dated Apr. 25, 2012.

Non-final Office Action for U.S. Appl. No. 12/959,017, "Method of Identifying When a Patient Undergoing Hemodialysis Is At Increased Risk of Death", dated Dec. 18, 2013.

Non-final Office Action for U.S. Appl. No. 13/642,364, System and Method of Identifying When a Patient Undergoing Hemodialysis Is At Increased Risk of Death by a Logistic Regression Model, dated Aug. 20, 2014.

Non-final Office Action for U.S. Appl. No. 13/642,364, System and Method of Identifying When a Patient Undergoing Hemodialysis Is At Increased Risk of Death by a Logistic Regression Model, dated Mar. 12, 2015.

Non-final Office Action for U.S. Appl. No. 13/642,364, System and Method of Identifying When a Patient Undergoing Hemodialysis Is At Increased Risk of Death by a Logistic Regression Model, dated Nov. 4, 2016.

Notice of Abandonment for U.S. Appl. No. 12/587,941, "Method of Identifying When a Patient Undergoing Hemodialysis Is At Increased Risk of Death", dated Sep. 19, 2012.

Notice of Allowance for U.S. Appl. No. 12/959,017, "Method of Identifying When a Patient Undergoing Hemodialysis Is At Increased Risk of Death", dated Jun. 8, 2017.

(56) References Cited

OTHER PUBLICATIONS

Panel Decision for U.S. Appl. No. 13/642,364, System and Method of Identifying When a Patient Undergoing Hemodialysis Is At Increased Risk of Death by a Logistic Regression Model, dated Oct. 12, 2016.
Advisory Action for U.S. Appl. No. 13/642,364, System and Method of Identifying When a Patient Undergoing Hemodialysis Is At Increased Risk of Death by a Logistic Regression Model, dated Dec. 4, 2017.
Non-final Office Action for U.S. Appl. No. 13/642,364, System and Method of Identifying When a Patient Undergoing Hemodialysis Is At Increased Risk of Death by a Logistic Regression Model, dated Feb. 16, 2018.
Notice of Allowance for U.S. Appl. No. 12/959,017, "Method of Identifying When a Patient Undergoing Hemodialysis Is At Increased Risk of Death", dated Sep. 20, 2017.
Panel Decision for U.S. Appl. No. 12/959,017, "Method of Identifying When a Patient Undergoing Hemodialysis Is At Increased Risk of Death", dated Mar. 20, 2017.

* cited by examiner

METHOD OF IDENTIFYING WHEN A PATIENT UNDERGOING HEMODIALYSIS IS AT INCREASED RISK OF DEATH

RELATED APPLICATION(S)

This application is the U.S. National Stage of International Application No. PCT/US2011/062774, filed Dec. 1, 2011, which designates the United States, is published in English, and claims the benefit of U.S. Provisional Application No. 61/419,089, filed Dec. 2, 2010. The entire teachings of the above applications are incorporated herein by reference.

BACKGROUND OF THE INVENTION

Despite significant advances in hemodialysis (HD) technology, the mortality risk of chronic HD patients remains well above that seen in the general population. The average remaining life expectancy in the general population is about 4 times higher than in dialysis patients, and the adjusted rates of all-cause mortality are 6.7 to 8.5 times higher for dialysis patients than in the general population. Cardiovascular disease and infectious disease are among the leading causes of mortality, and the overall annual mortality rate in dialysis patients is about 20% in the United States. See United States Renal Data System, USRDS 2009 Annual Data Report, National Institutes of Health.

Current epidemiologic studies seeking to investigate the determinants of mortality risk in dialysis patients usually consider either cross-sectional baseline characteristics (e.g., mean systolic blood pressure in the first 3 months after start of dialysis, serum albumin levels after 6 months) or time-dependent analyses, most commonly time-dependent Cox regression models. Patients are frequently stratified into groups based on descriptive characteristics such as tertiles. In many of these studies, the first date of dialysis is taken as the reference point.

Despite such improvements in hemodialysis technology and patient tracking, chronic hemodialysis patients continue to experience an inordinately high mortality rate. Therefore, there is a need for an improved method of identifying hemodialysis patients at increased risk of death, in order to trigger earlier diagnostic and therapeutic interventions and consequently reduce patient mortality.

SUMMARY OF THE INVENTION

The present invention is directed to a method of identifying a patient undergoing periodic hemodialysis treatments at increased risk for death. The method includes determining at least one of the patient's clinical or biochemical parameters associated with an increased risk of death, consisting of serum bicarbonate concentration level, serum potassium concentration level, serum calcium concentration level, hemoglobin concentration level, serum phosphorus concentration level, neutrophil to lymphocyte ratio, equilibrated normalized protein catabolic rate (enPCR), equilibrated fractional clearance of total body water by dialysis and residual kidney function (eKdrt/V), Erythropoietin (EPO) resistance index, transferrin saturation index (TSAT), serum ferritin concentration level, serum creatinine concentration level, platelet count, Aspartat-Aminotransferase level, and Alanin-Aminotransferase level, periodically while the patient is undergoing hemodialysis treatments, and identifying a patient as having an increased risk for death if the patient has a significant change in the rate of change of at least one of these clinical or biochemical parameters. A significant change can be determined by using a statistical method, or defined as a change from a steady level to an increase or decrease, or a change in character of the rate of change of the at least one clinical or biochemical parameter. Identifying the patient as having an increased risk of death is accomplished within a sufficient lead time to allow for a therapeutic intervention to decrease the patient's risk of death, followed by a suitable therapeutic intervention.

The present invention is also directed to a method of identifying an increased mortality risk factor for a patient undergoing periodic hemodialysis treatment. The method includes analyzing data of deceased patients that were previously undergoing periodic hemodialysis treatments by performing a longitudinal analysis backwards in time of changes in a clinical or biochemical parameter of the patients, and identifying a significant change in the rate of decline or the rate of increase of one or more clinical or biochemical parameters before death of the patients.

The methods of this invention enable physicians and/or other health-care professionals to initiate timely diagnostic and therapeutic interventions to hemodialysis patients at increased risk of death and thereby reduce mortality of such patients.

BRIEF DESCRIPTION OF THE DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

DETAILED DESCRIPTION OF THE INVENTION

Figure 1:
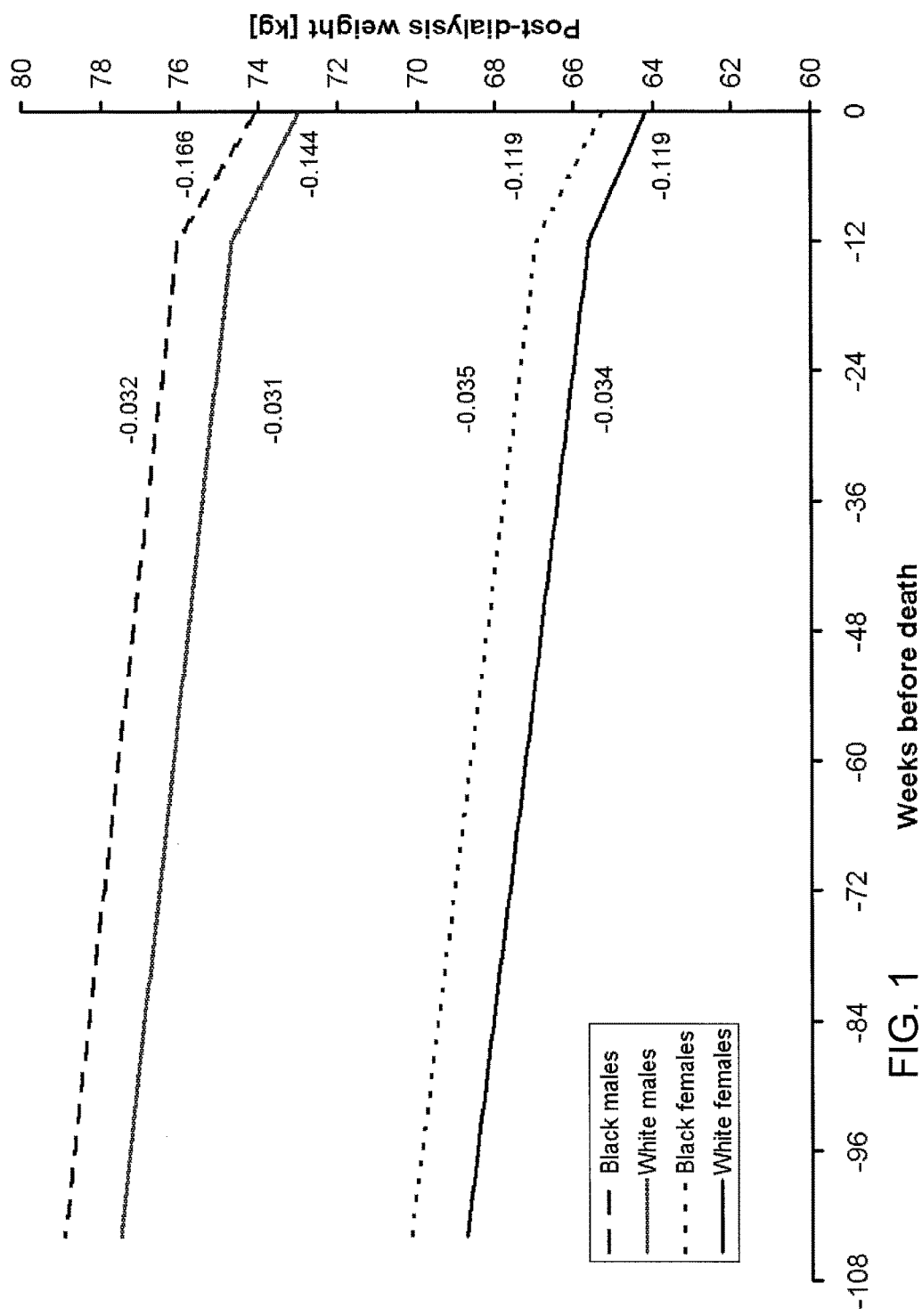
FIG. 1 is a graph of linear splines of post-dialysis body weight of hemodialysis patients as a function of time before death; knot point at 12 weeks before death.

The present invention is directed to a method of identifying a patient at increased risk for death when the patient is undergoing periodic hemodialysis treatments. The method includes determining at least one of the patient's clinical or biochemical parameters associated with an increased risk of death, consisting of serum bicarbonate concentration level, serum potassium concentration level, serum calcium concentration level, hemoglobin concentration level, serum phosphorus concentration level, neutrophil to lymphocyte ratio, equilibrated normalized protein catabolic rate (enPCR), equilibrated fractional clearance of total body water by dialysis and residual kidney function (eKdrt/V), Erythropoietin (EPO) resistance index, transferrin saturation index (TSAT), ferritin, serum creatinine concentration level, platelet count, Aspartat-Aminotransferase level, and Alanin-Aminotransferase level at periodic hemodialysis treatments. The patient is identified as having an increased risk for death if the patient has a significant change in the rate of change of at least one of these clinical or biochemical parameters. A significant change can be determined by using a statistical method, such as using Student's t as the test statistic (e.g., $p<0.05$), or defined as a change from a steady level (e.g., no significant deviation form an average of the measured levels) to an increase or decrease, or a change in character (e.g., a change from increase to decrease or vice versa, or a change from a steady level to increase or decrease) in the rate of change of the at least one clinical or biochemical parameter. The measurement of at least one of these clinical or biochemical parameters includes the measurement of any combination of them. In a preferred embodiment, a determination that the rate of change of a clinical or biochemical parameter of the patient has changed character is employed to identify a patient at increased risk of death.

The method is applied to a patient that is undergoing periodic hemodialysis treatments. Typically, periodic hemodialysis treatments are performed several days apart, for example, three times per week. The time period between treatments is not necessarily constant, however, because, for example, the patient can receive treatment after a shorter time period since the last treatment if the patient needs to shed excess fluid. The time period between treatments can be longer because of, for example, missed treatments or an illness acquired since the last treatment.

The methods of this invention apply to human patients that are undergoing hemodialysis treatment. The hemodialysis treatment of the patient is a treatment that replaces or supplements the normal function of the kidneys of a patient, due to the patient having a disease or condition that affects kidney function such as, for example, renal insufficiency, renal failure, or kidney disease.

The measurements of the patient's systolic blood pressure, serum albumin concentration level, body weight, body temperature, serum bicarbonate concentration level, serum potassium concentration level, serum calcium concentration level, hemoglobin concentration level, serum phosphorus concentration level, neutrophil to lymphocyte ratio, equilibrated normalized protein catabolic rate (enPCR), equilibrated fractional clearance of total body water by dialysis and residual kidney function (eKdrt/V), Erythropoietin (EPO) resistance index, transferrin saturation index (TSAT), serum ferritin concentration level, serum creatinine concentration level, platelet count, Aspartat-Aminotransferase level, and Alanin-Aminotransferase level are obtained using methods well known in the art. The measurements of the aforementioned clinical or biochemical parameters can be performed either before or after each hemodialysis treatment, or both, or only performed after a certain time period, or at every certain number of treatments, or at irregular intervals. For example, the measurement of systolic blood pressure is usually taken before each treatment, but can also be taken after each treatment, or both before and after each treatment. The measurement of serum albumin concentration level is usually taken once a month, but can also be taken more often. The measurement of body weight is usually taken before each treatment, but can also be taken after each treatment. The measurement of body temperature is preferentially taken before each treatment, but can also be taken after each treatment. Of course, the measurements of the patient's clinical and biochemical parameters could also be taken between hemodialysis treatments.

The importance of determining a significant change in the rate of change of the patient's systolic blood pressure, serum albumin concentration level, body weight, body temperature, serum bicarbonate concentration level, serum potassium concentration level, serum calcium concentration level, hemoglobin concentration level, serum phosphorus concentration level, neutrophil to lymphocyte ratio, equilibrated normalized protein catabolic rate (enPCR), equilibrated fractional clearance of total body water by dialysis and residual kidney function (eKdrt/V), Erythropoietin (EPO) resistance index, transferrin saturation index (TSAT), ferritin, serum creatinine concentration level, platelet count, Aspartat-Aminotransferase level, and Alanin-Aminotransferase level was uncovered by focusing specifically on the time-course of these clinical or biochemical parameters before death in a large sample of hemodialysis patients. In this analysis, the reference point for the analysis was the patient's date of death, and the analysis looked back in time from that point, in order to uncover what changes in clinical or biochemical parameters preceded demise. This retrospective record review included a data set of 2,462 in-center maintenance HD patients who expired between Jul. 1, 2005 and Apr. 30, 2008. Patients' monthly serum albumin concentration levels were compiled for the 24 months preceding the date of death. Similarly, the median weekly post-dialysis weight was compiled for the 104 weeks prior to death. Causes of death (COD), recorded using ICD-9 codes, were retrieved from patient record sheets. *See The International Classification of Diseases, 9th Revision, Clinical Modification,* (ICD-9-CM), National Center for Health Statistics and Centers for Medicare & Medicaid Services (2007). Three broad COD categories (cardiovascular, cerebrovascular, and infectious) were included in the analyses. Going back in time allowed an analysis of events occurring in the days, weeks, and months prior to demise. This is, in principle, a longitudinal data analysis backwards in time with death as the common end point. The defining feature of such a longitudinal analysis is that measurements of the same individual are taken repeatedly over time, thereby allowing the direct study of change over time. Measurement variability stems from three sources: between-subject heterogeneity, within-subject variability, and (random) measurement errors. With repeated measurements available, the individual patients' changes in responses over time can be studied. In addition, the mean response of a group of parameters (for example, gender, race, co-morbidities) can be modeled.

The longitudinal analysis of patient clinical or biochemical parameters was conducted using linear mixed effects models (LMMs). LMMs form a broad class of models which handle longitudinal data in a very general setting (e.g., the data can be unbalanced and mis-timed). See G. M. Fitzmaurice, N. M. Laird, and J. H. Ware, *Applied Longitudinal Analysis,* (2004). In the LMMs employed, individual patient effects can be separated from population effects by treating the individual effects as random, while the population effects are regarded as fixed; the full model combines the random and the fixed effects. A powerful result is that subject response trajectories can be estimated in addition to the population response trajectory. In this application, a random intercept model was used. In this model, each subject has a distinct level of response which persists over time. The patient serves as his or her own control insofar as the dynamics between observed time periods are compared. To determine which random effects should be included in the models, the Bayesian information criterion (BIC) was used; this measure rewards a model with higher explanatory power, while penalizing for the inclusion of additional parameters. In this data analysis, the data were fit by linear spline functions, because these simple parametric curves can provide a parsimonious description of longitudinal trends. See D. Ruppert, M. P. Wand, and R. J. Carroll, *Semiparametric Regression,* (2003). Linear spline functions with a knot point at 12 weeks before death were employed for systolic blood pressure, body weight, and body temperature. A knot point is the point in time where two spline functions intersect. The choice of the location for the knot point is important with this kind of analysis. The knot point (12 weeks before death) was chosen by separating the data into two sets for processing, one data set including all the data up to 12 weeks before death, and the other data set including the data from 12 weeks before death to the patient's demise. The knot point (12 weeks before death) was chosen for the following reasons: (a) based on pilot descriptive data analysis which revealed an accelerated deterioration of body weight in the 12 weeks preceding death, and (b) because it was deemed that a lead time of 12 weeks was probably sufficient to intervene in many patients.

The time point chosen as the knot point generally depends on the clinical or biochemical parameter being analyzed, to provide sufficient time for an effective diagnostic or therapeutic patient intervention. The knot point was chosen at 3 months for the other clinical or biochemical parameters discussed below, because the measurements of those parameters are typically obtained at one month intervals.

Turning now to FIG. 1, the results for post-dialysis body weight, typically measured in kg, are shown for the data set. Four groups of dialysis patients, black and white males and females, all showed an increase in the rate of decrease of post-dialysis body weight in the final 12 weeks of life, from about 0.03 kg/week to over about 0.1 kg/week. Therefore, in this study, for post-dialysis body weight, the rate of decrease increased by a factor of about 3 in the final 12 weeks of life.

Figure 2:
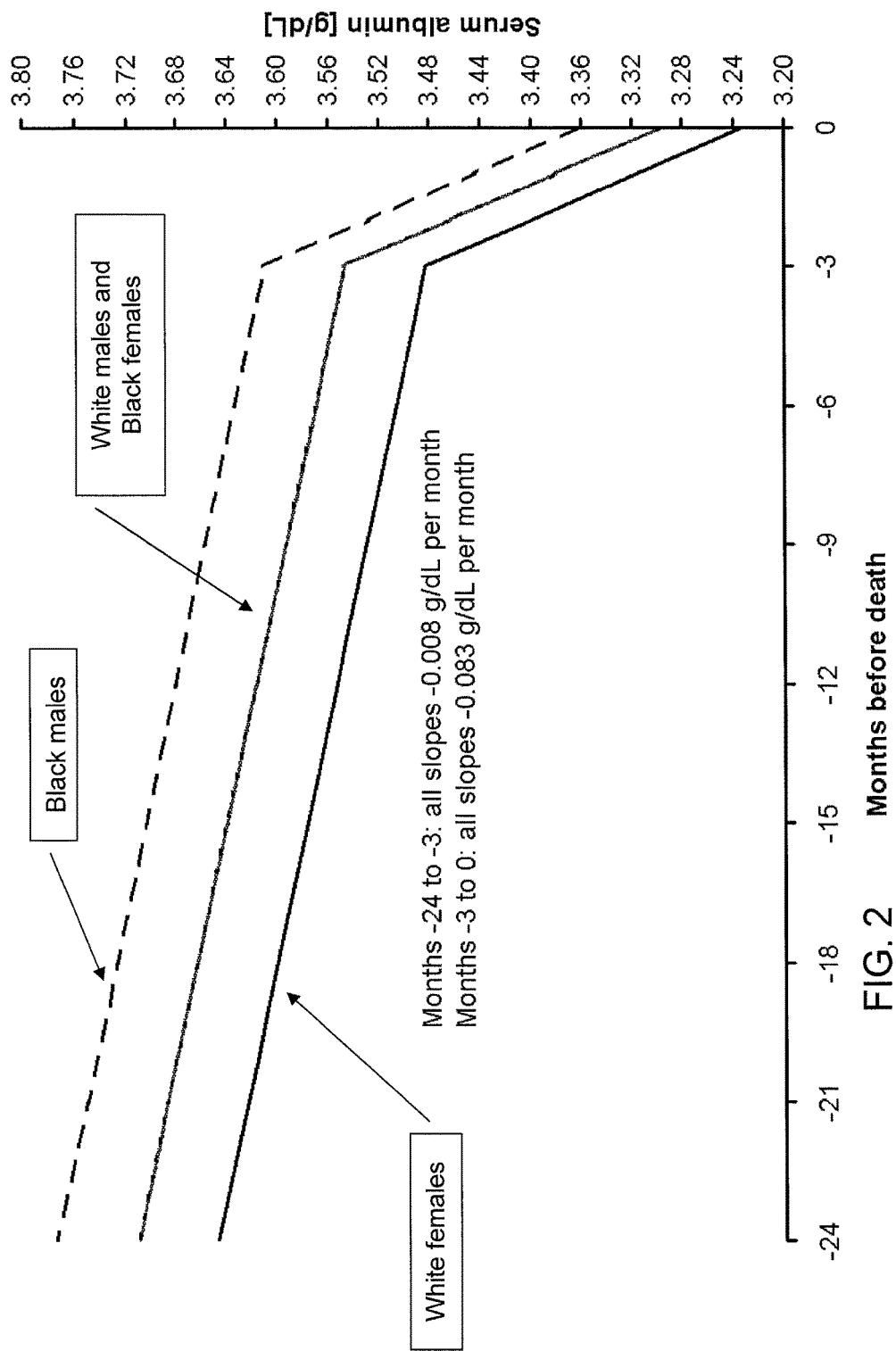
FIG. 2 is a graph of linear splines of serum albumin concentration levels of hemodialysis patients as a function of time before death; knot point at 3 months before death.

Turning now to FIG. 2, the results for serum albumin concentration levels, typically measured in g/dL, are shown for the data set. The four groups of dialysis patients showed an increase in the rate of decline of serum albumin levels in the final 3 months of life, from about 0.008 g/dL/month to over about 0.08 g/dL/month. Therefore, in this study, for serum albumin levels, the rate of decrease increased by a factor of about 10 in the final 3 months of life.

Figure 3:
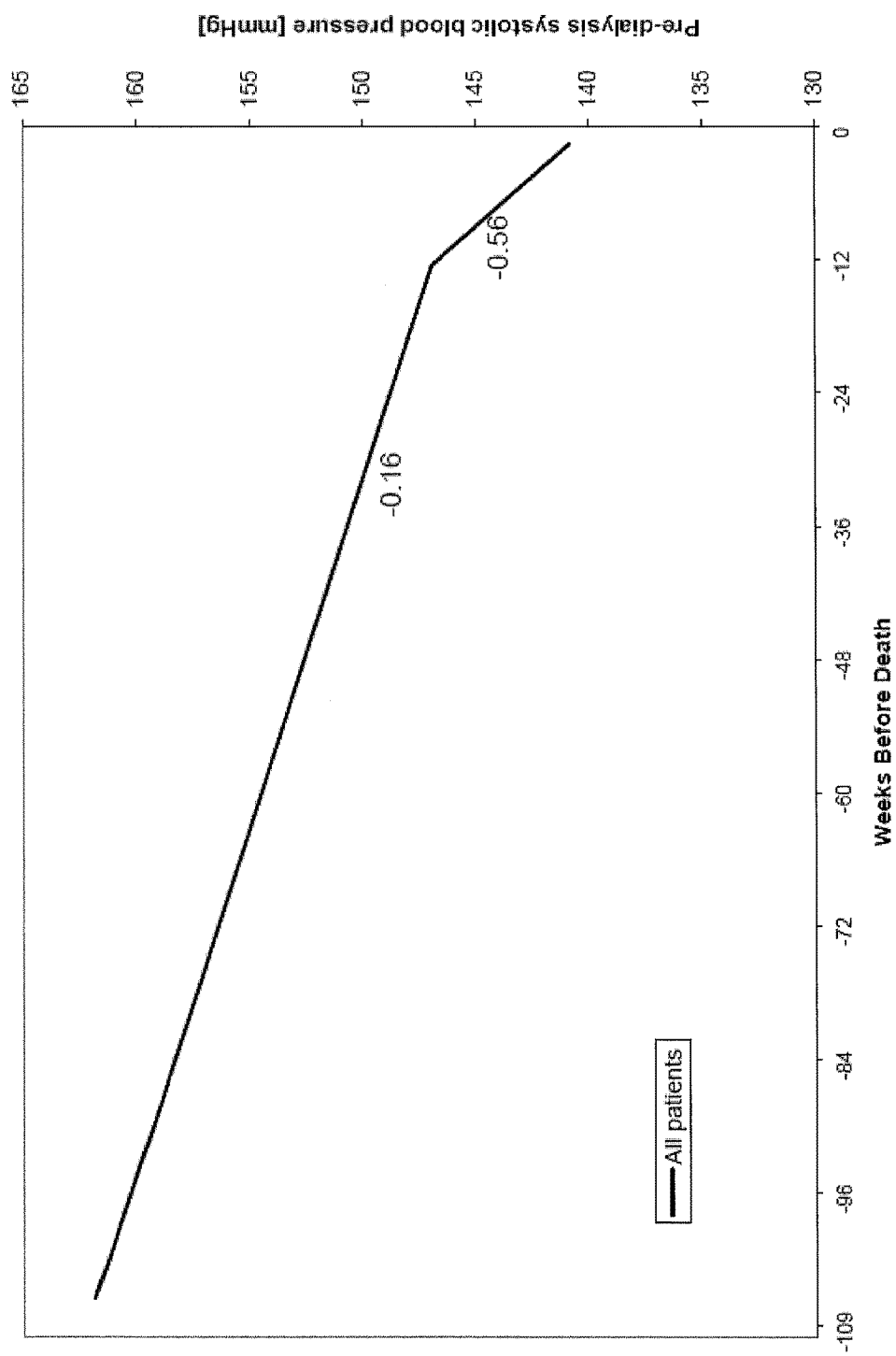
FIG. 3 is a graph of linear splines of systolic blood pressure of hemodialysis patients as a function of time before death; knot point at 12 weeks before death.

Turning now to FIG. 3, in a separate study of 1,799 hemodialysis patients, it was found that the average pre-dialysis systolic blood pressure of patients, typically measured in mmHg, showed an increase in the rate of decrease in the final 12 weeks of life, from about 0.16 mmHg/week to about 0.56 mmHg/week. Therefore, in this study, for pre-dialysis systolic blood pressure, the rate of decrease increased by a factor of about 3 in the final 12 weeks of life.

Figure 4:
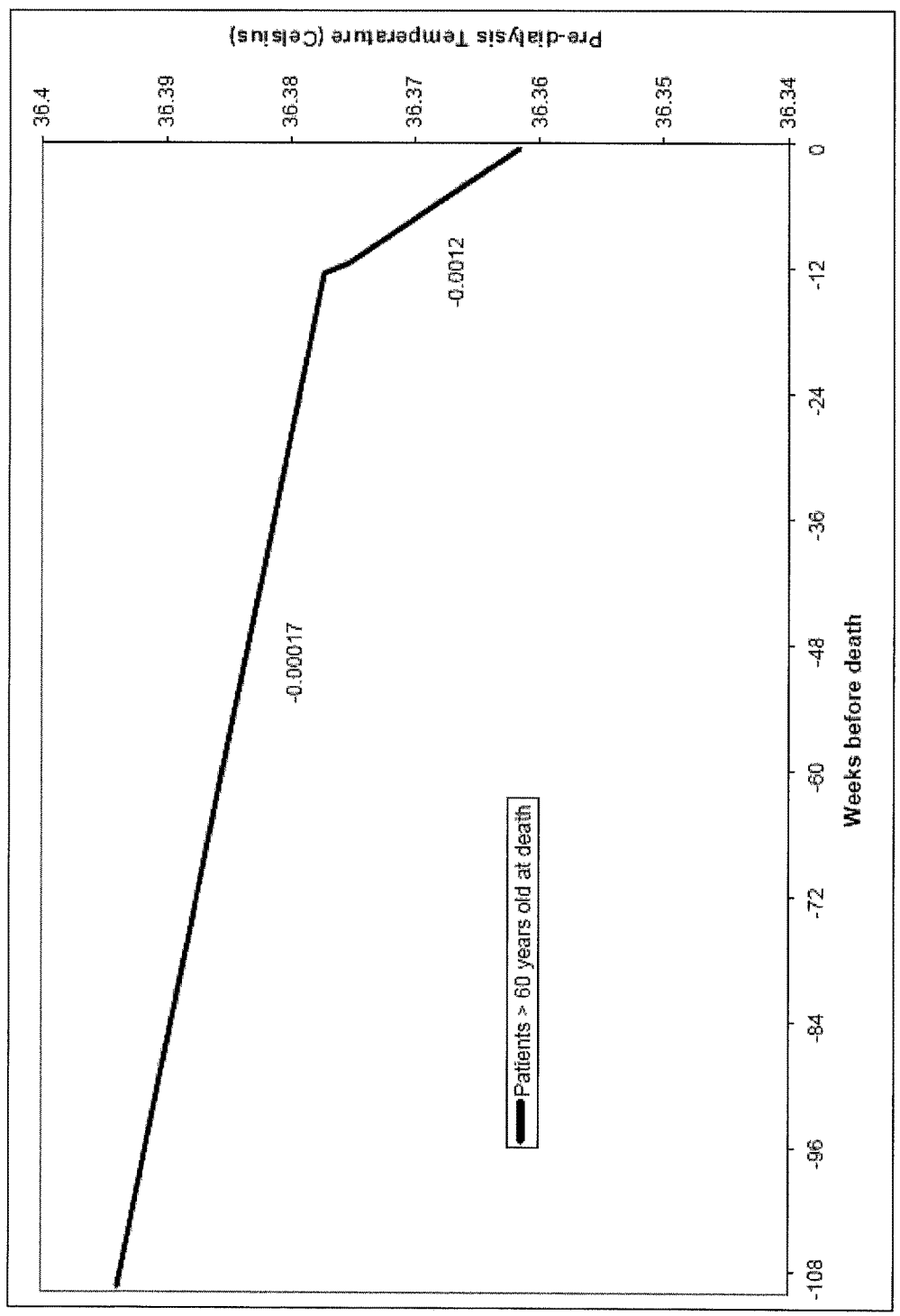
FIG. 4 is a graph of linear splines of body temperature of hemodialysis patients (age>60 years old at death) as a function of time before death; knot point at 12 weeks before death.

Turning now to FIG. 4, in another study of hemodialysis patients over 60 years old at death, it was found that the pre-dialysis body temperature of patients, typically measured in ° C., showed an increase in the rate of decline in the final 12 weeks of life, from about 0.00017° C./week to about 0.0012° C./week. Therefore, in this study, for body temperature, the rate of decrease increased by a factor of about 7 in the final 12 weeks of life.

Figure 5:
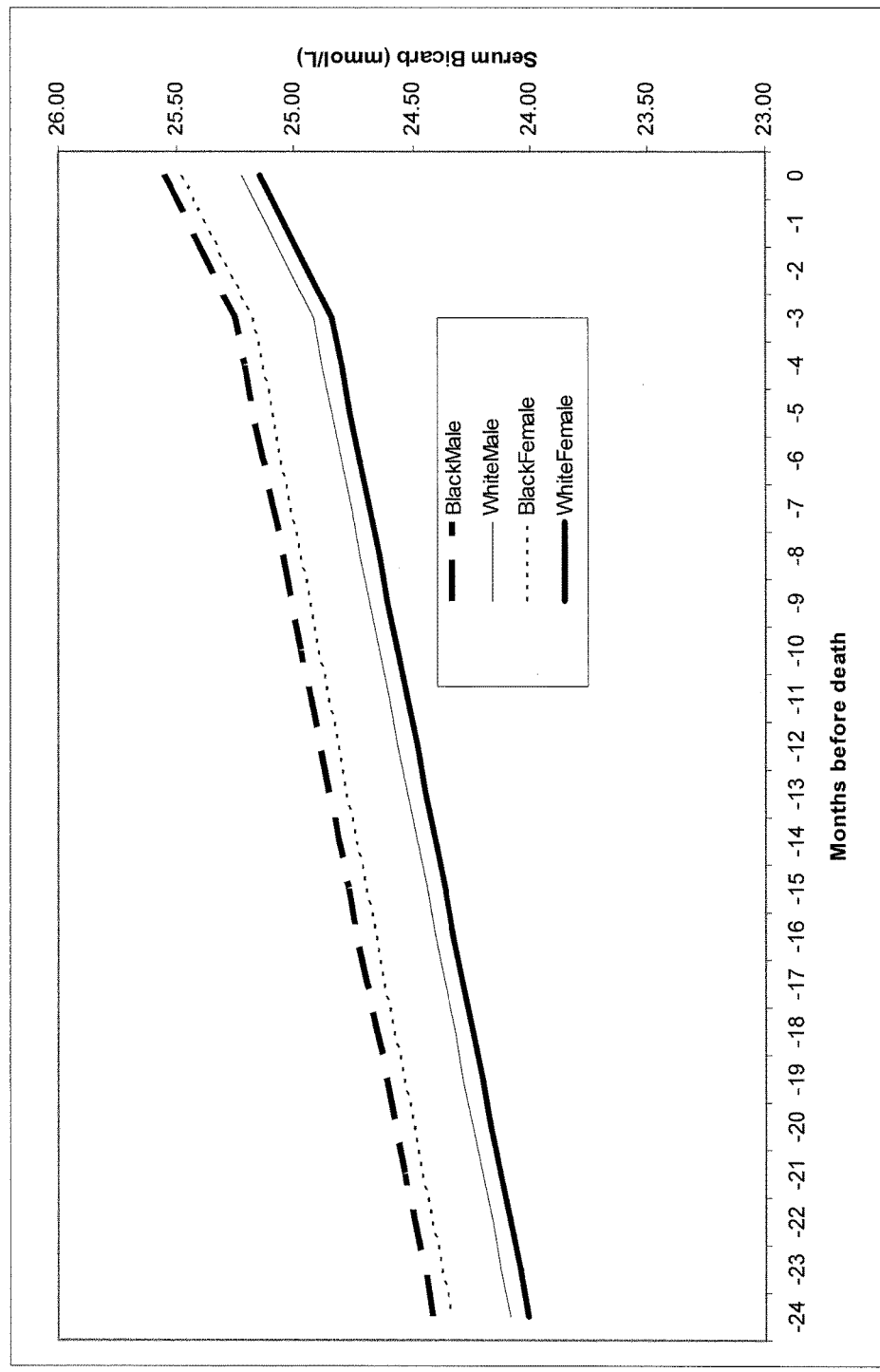
FIG. 5 is a graph of linear splines of serum bicarbonate concentration levels of hemodialysis patients as a function of time before death; knot point at 3 months before death.

Turning now to FIG. 5, in another study of hemodialysis patients, it was found that the serum bicarbonate concentration levels of patients, typically measured in mmol/L, showed an increase in the rate of increase in the final 3 months of life, from about 0.040 mmol/L/month to about 0.101 mmol/L/month. Therefore, in this study, for serum bicarbonate level, the rate of increase increased by a factor of over 2 in the final 3 months of life. Bicarbonate is a crucial component of the body's acid-base metabolism. Higher bicarbonate concentration levels may point toward a metabolic alkalosis, which could be caused by reduced ingestion of protein.

Figure 6:
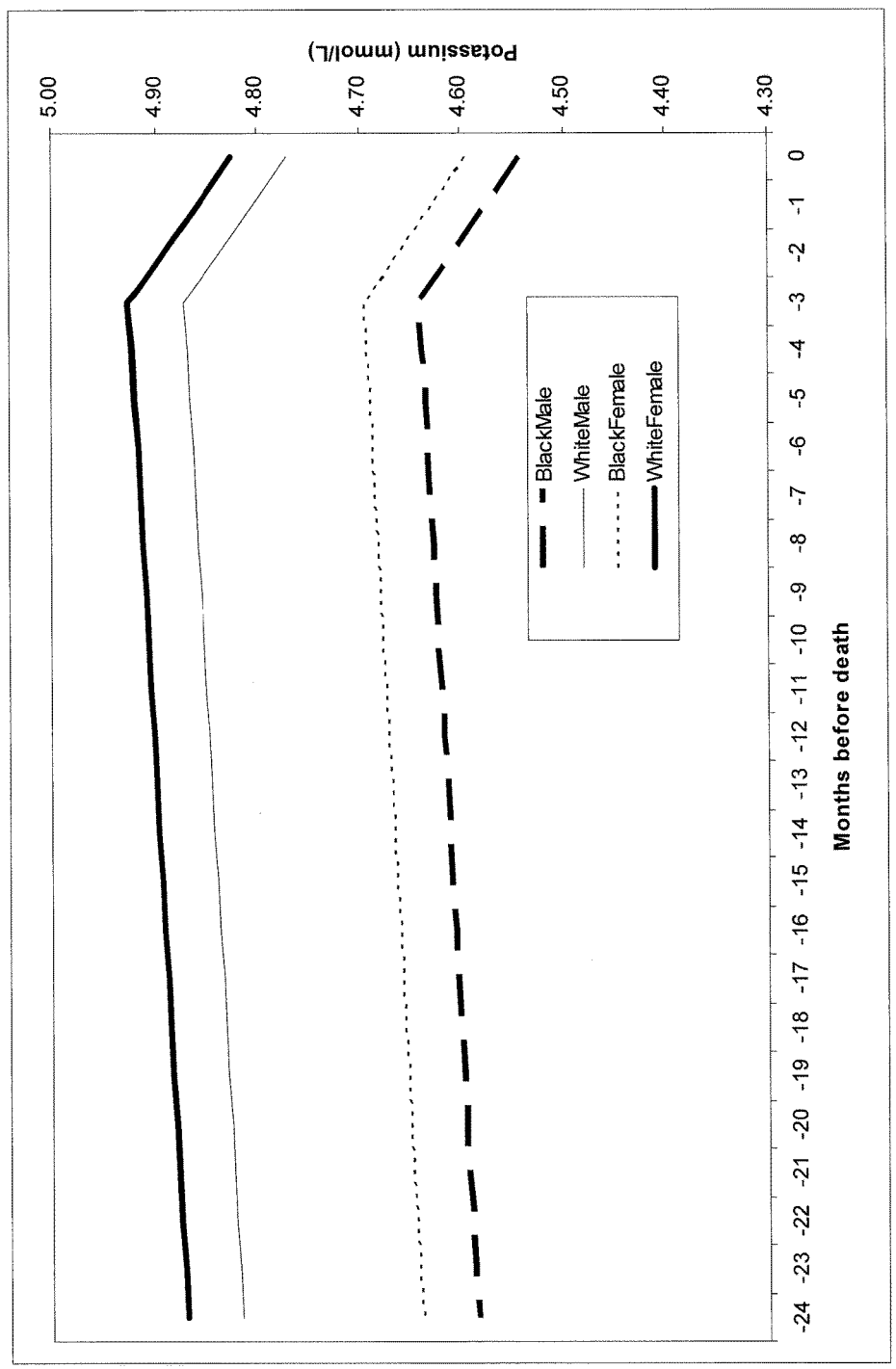
FIG. 6 is a graph of linear splines of serum potassium concentration levels of hemodialysis patients as a function of time before death; knot point at 3 months before death.

Turning now to FIG. 6, it was found that the serum potassium concentration levels of patients, typically measured in mmol/L, showed a change in the rate of change in the final 3 months of life, from an increase of about 0.003 mmol/L/month to a decrease of about 0.033 mmol/L/month. Therefore, in this study, for serum potassium concentration level, the rate of change altered character (from increase to decrease) in the final 3 months of life. Potassium is crucial for the electrical potential of cells. A decrease in potassium concentration is seen with poor nutrition and with metabolic alkalosis.

Figure 7:
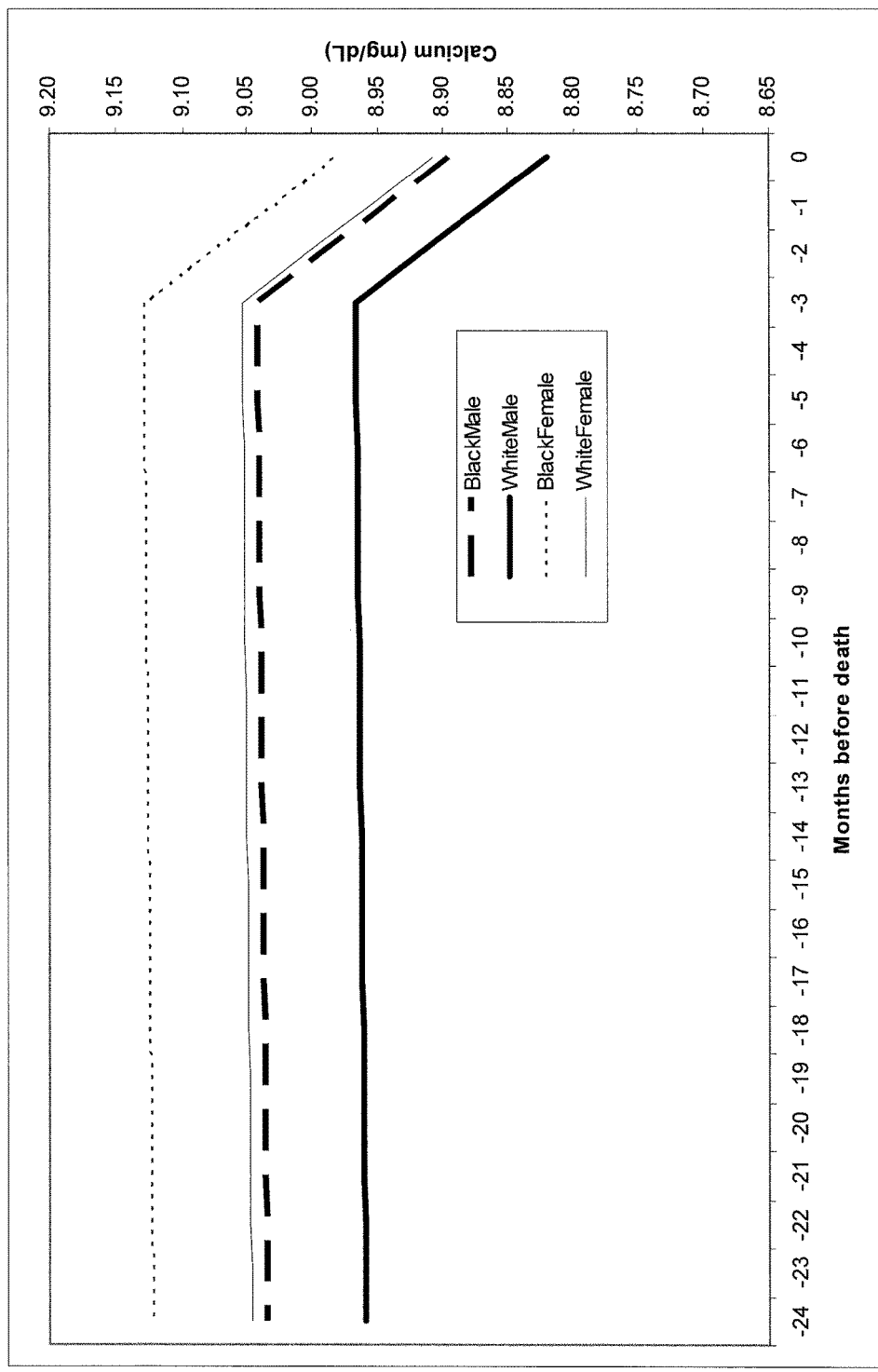
FIG. 7 is a graph of linear splines of serum calcium concentration levels of hemodialysis patients as a function of time before death; knot point at 3 months before death.

Turning now to FIG. 7, it was found that the serum calcium concentration levels of patients, typically measured in g/dL, showed a change in the rate of change in the final 3 months of life, from a steady level to a significant decrease of about 0.049 g/dL/month. Therefore, in this study, for serum calcium concentration level, the rate of change significantly increased in the final 3 months of life. Calcium is an essential component for muscle contraction. A decrease in total calcium concentration is seen with a decrease in serum albumin concentration levels.

Figure 8:
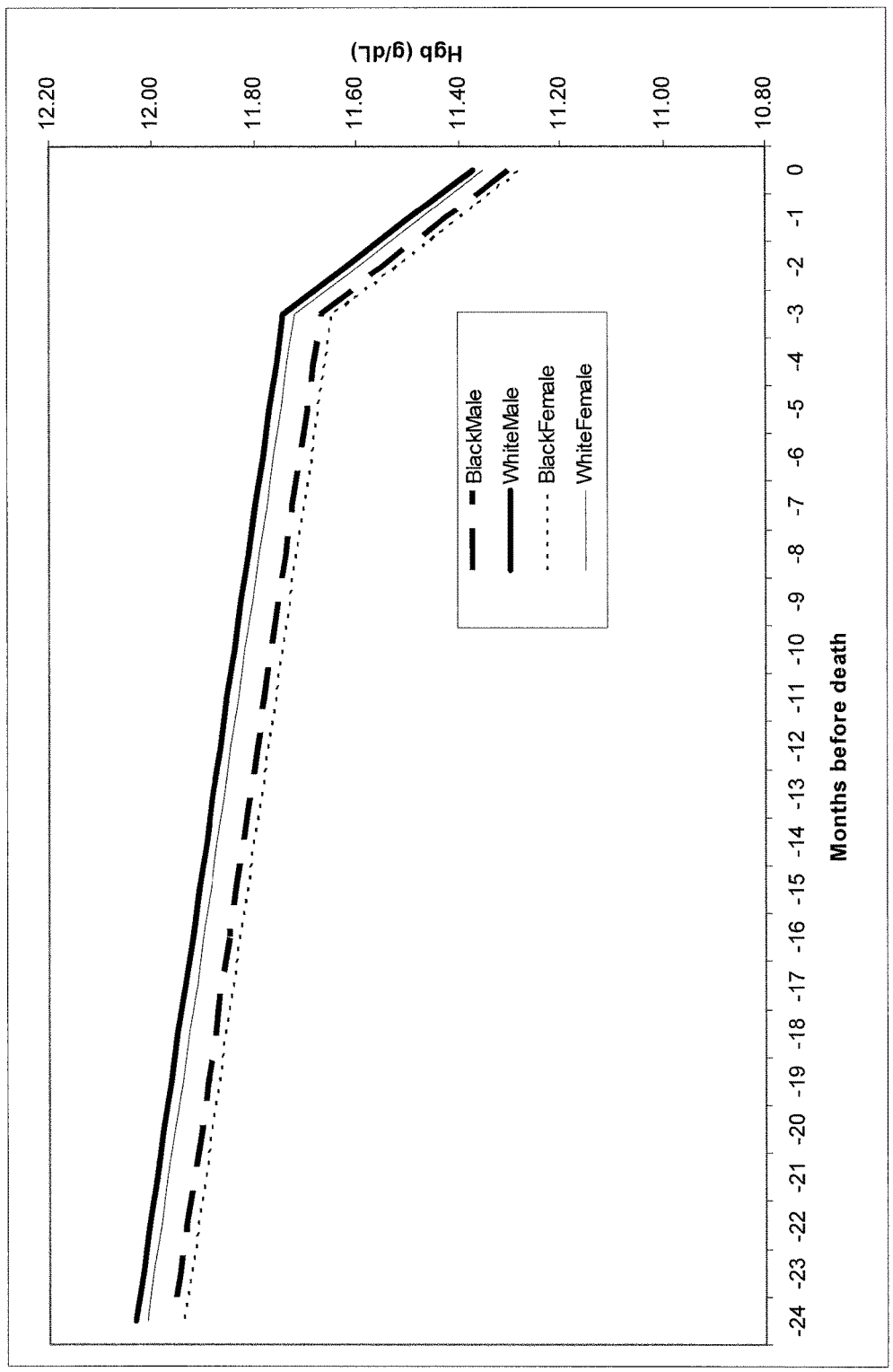
FIG. 8 is a graph of linear splines of hemoglobin (Hgb) concentration levels of hemodialysis patients as a function of time before death; knot point at 3 months before death.

Turning now to FIG. 8, it was found that the hemoglobin (Hgb) concentration levels of patients, typically measured in g/dL, showed a change in the rate of decrease in the final 3 months of life, from a decrease of about 0.014 g/dL/month to a decrease of about 0.123 g/dL/month. Therefore, in this study, for hemoglobin concentration level, the rate of decrease increased by a factor of about 8 in the final 3 months of life. Hemoglobin concentration levels describe the degree of anemia. A decrease in hemoglobin concentration level is associated with inflammation, bleeding, or iron deficiency.

Figure 9:
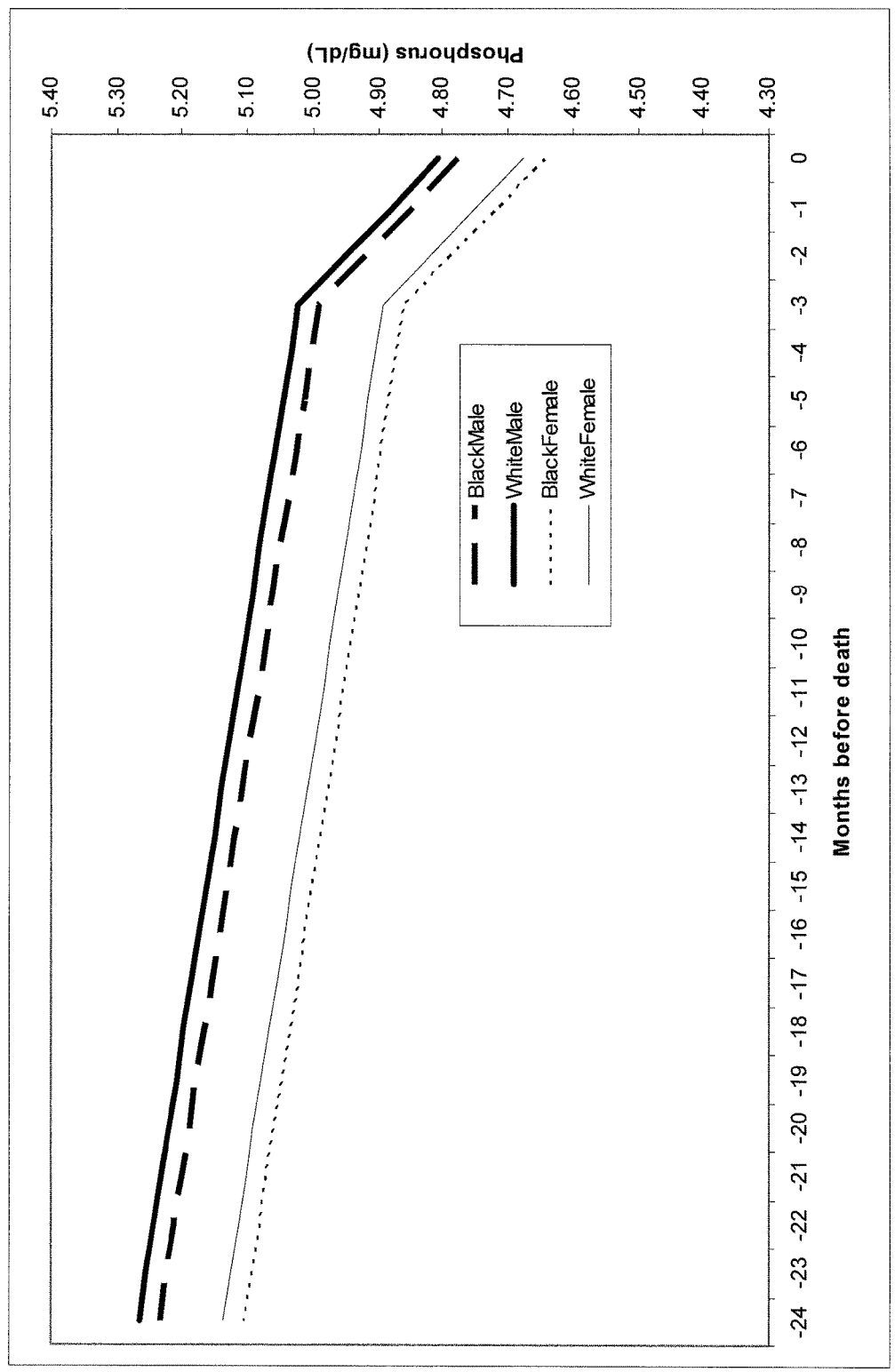
FIG. 9 is a graph of linear splines of serum phosphorus concentration levels of hemodialysis patients as a function of time before death; knot point at 3 months before death.

Turning now to FIG. 9, it was found that the phosphorus concentration levels of patients, typically measured in mg/dL, showed a change in the rate of decrease in the final 3 months of life, from a decrease of about 0.012 mg/dL/month to a decrease of about 0.072 mg/dL/month. Therefore, in this study, for phosphorus concentration level, the rate of decrease increased by a factor of about 6 in the final 3 months of life. Phosphorus is a surrogate for nutritional intake of protein and an important component of bone and mineral metabolism.

Figure 10:
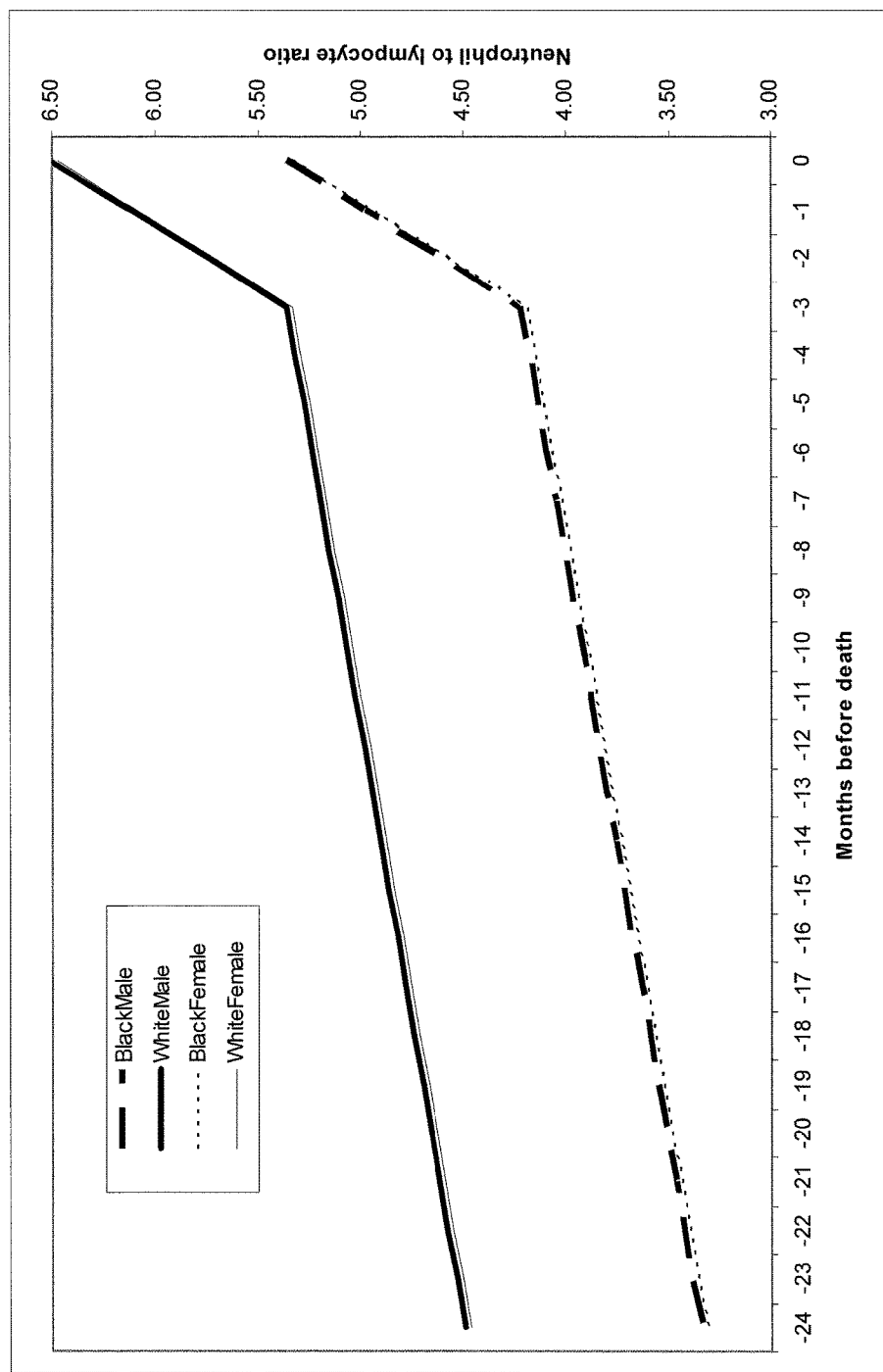
FIG. 10 is a graph of linear splines of neutrophil to lymphocyte ratio of hemodialysis patients as a function of time before death; knot point at 3 months before death.

Turning now to FIG. 10, it was found that the neutrophil to lymphocyte ratio of patients, a dimensionless number, showed a change in the rate of increase in the final 3 months of life, from a increase of about 0.042 per month to a increase of about 0.381 per month. Therefore, in this study, for neutrophil to lymphocyte ratio, the rate of increase increased by a factor of about 9 in the final 3 months of life. The neutrophil to lymphocyte ratio increases with inflammation.

Figure 11:
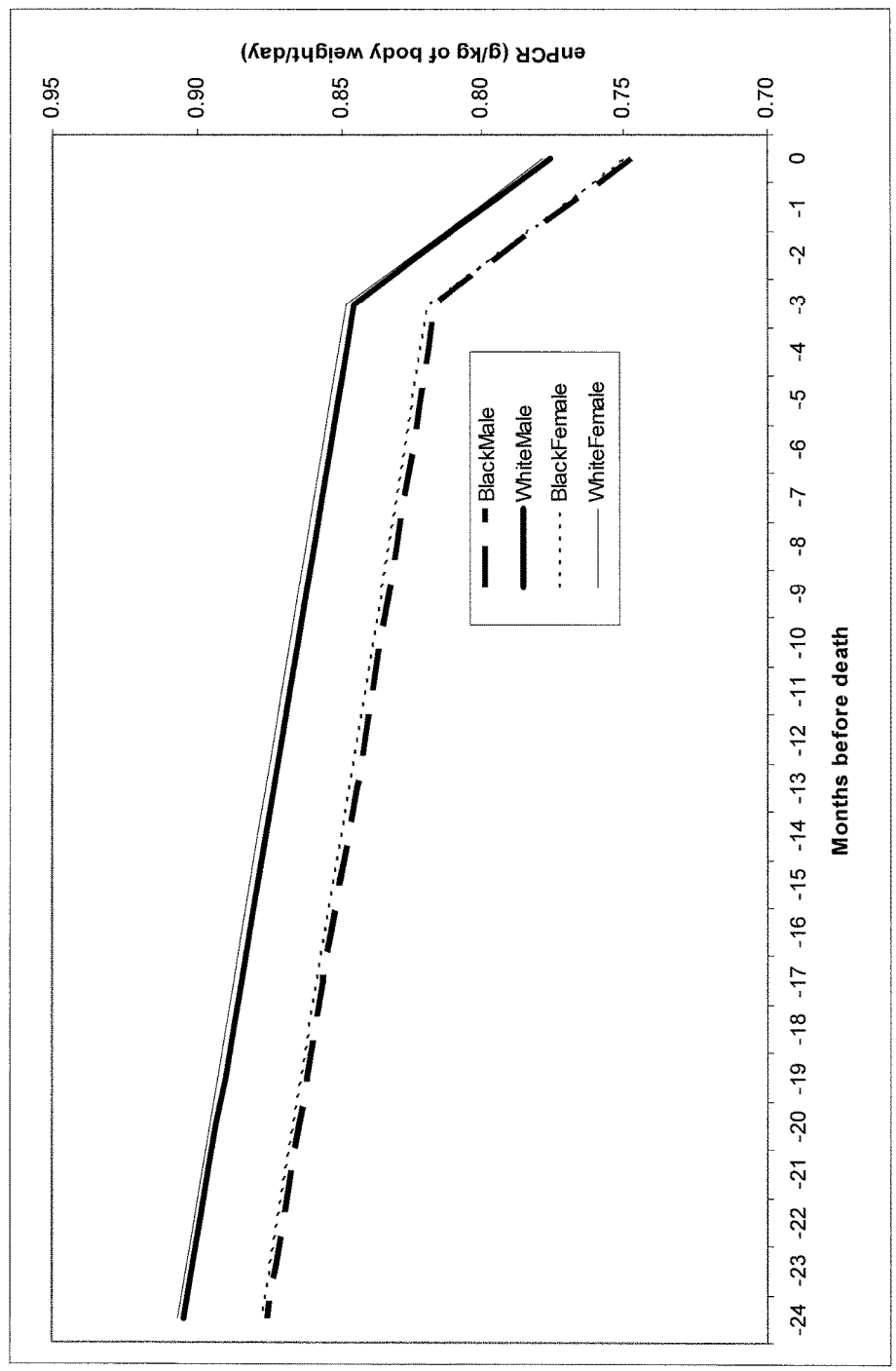
FIG. 11 is a graph of linear splines of enPCR of hemodialysis patients as a function of time before death; knot point at 3 months before death.

Turning now to FIG. 11, it was found that the enPCR of patients, typically measured in g/kg body weight/day, showed a change in the rate of decrease in the final 3 months of life, from a decrease of about 0.003 per month to a decrease of about 0.023 per month. Therefore, in this study, for enPCR, the rate of decrease increased by a factor of about 7 in the final 3 months of life. The enPCR is an estimate of daily protein intake.

Figure 12:
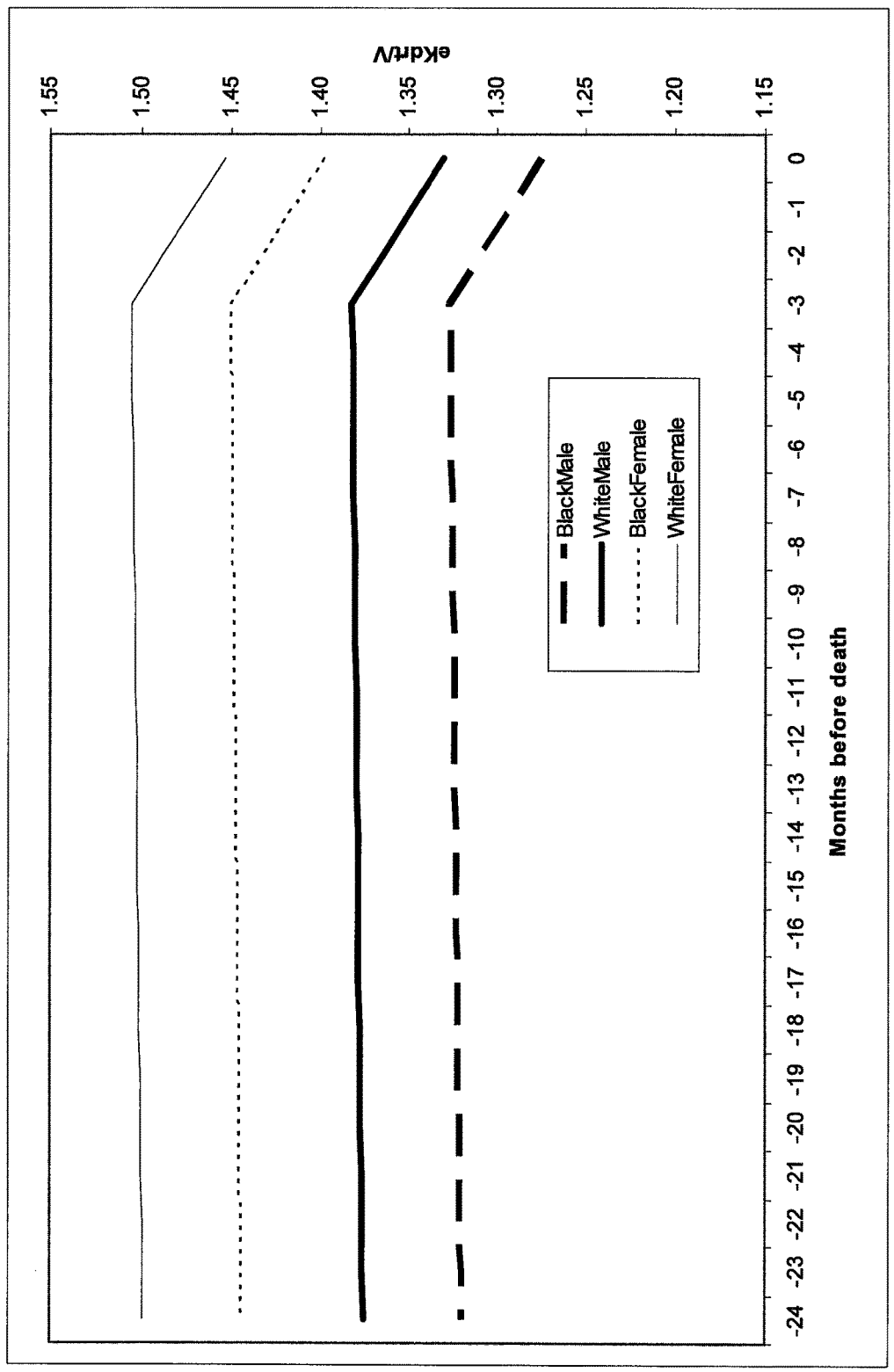
FIG. 12 is a graph of linear splines of eKdrt/V of hemodialysis patients as a function of time before death; knot point at 3 months before death.

Turning now to FIG. 12, it was found that the eKdrt/V of patients, a dimensionless number, showed a change in the rate of decrease in the final 3 months of life, from a steady level to a decrease of about 0.017 per month. Therefore, in this study, for eKdrt/V, the rate of decrease significantly increased in the final 3 months of life. The eKdrt/V is a measure of the clearance of urea and other low-molecular weight unbound solutes, taking the dialytic and renal component into account.

Figure 13:
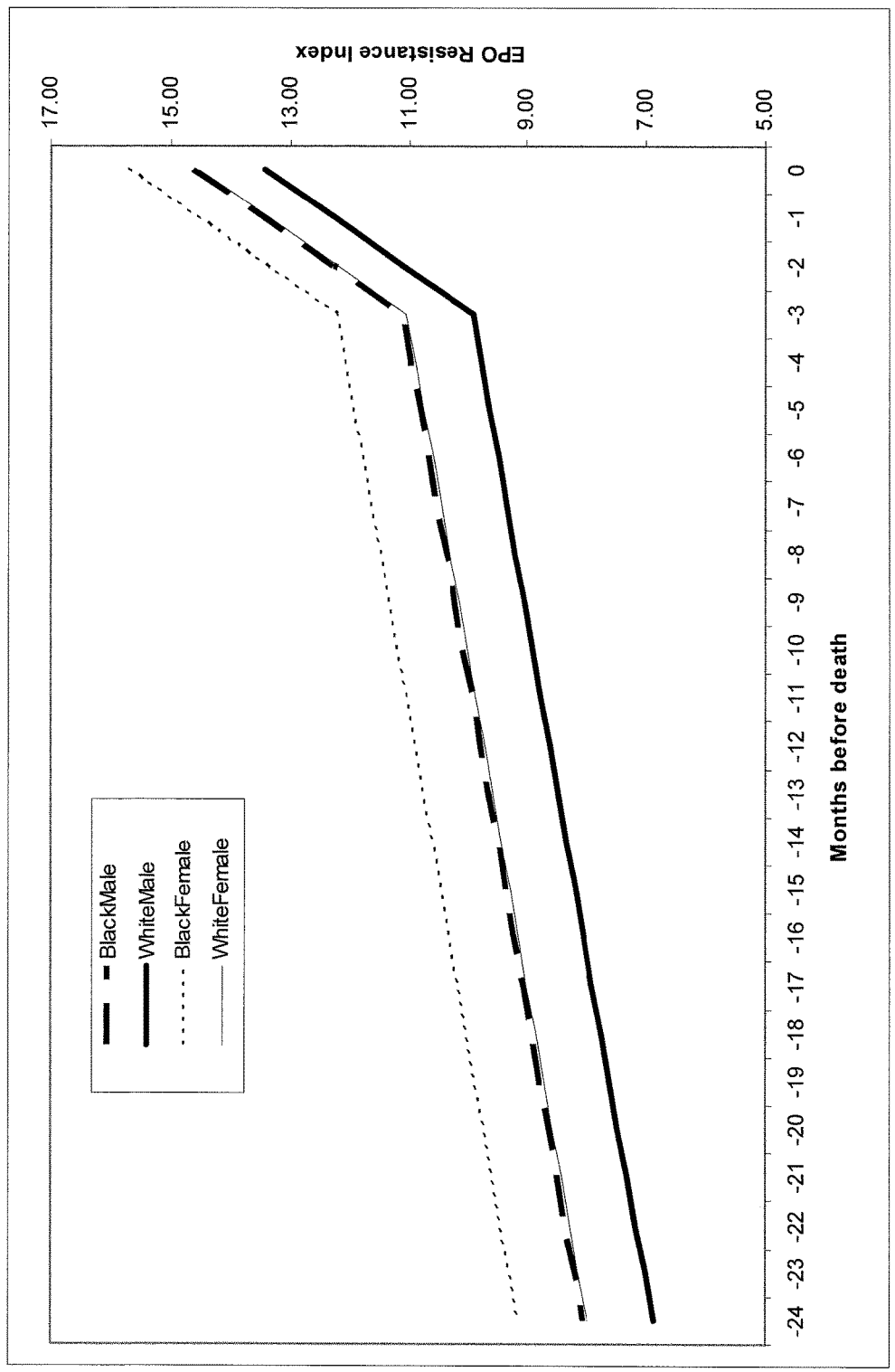
FIG. 13 is a graph of linear splines of EPO resistance index of hemodialysis patients as a function of time before death; knot point at 3 months before death.

Turning now to FIG. 13, it was found that the EPO resistance index of patients, typically measured in U/kg body weight per week, showed a change in the rate of increase in the final 3 months of life, from an increase of about 0.145 per month to an increase of about 1.169 per month. Therefore, in this study, for EPO resistance index, the rate of increase increased by a factor of about 8 in the final 3 months of life. A high EPO resistance index is an indication of inflammation.

Figure 14:
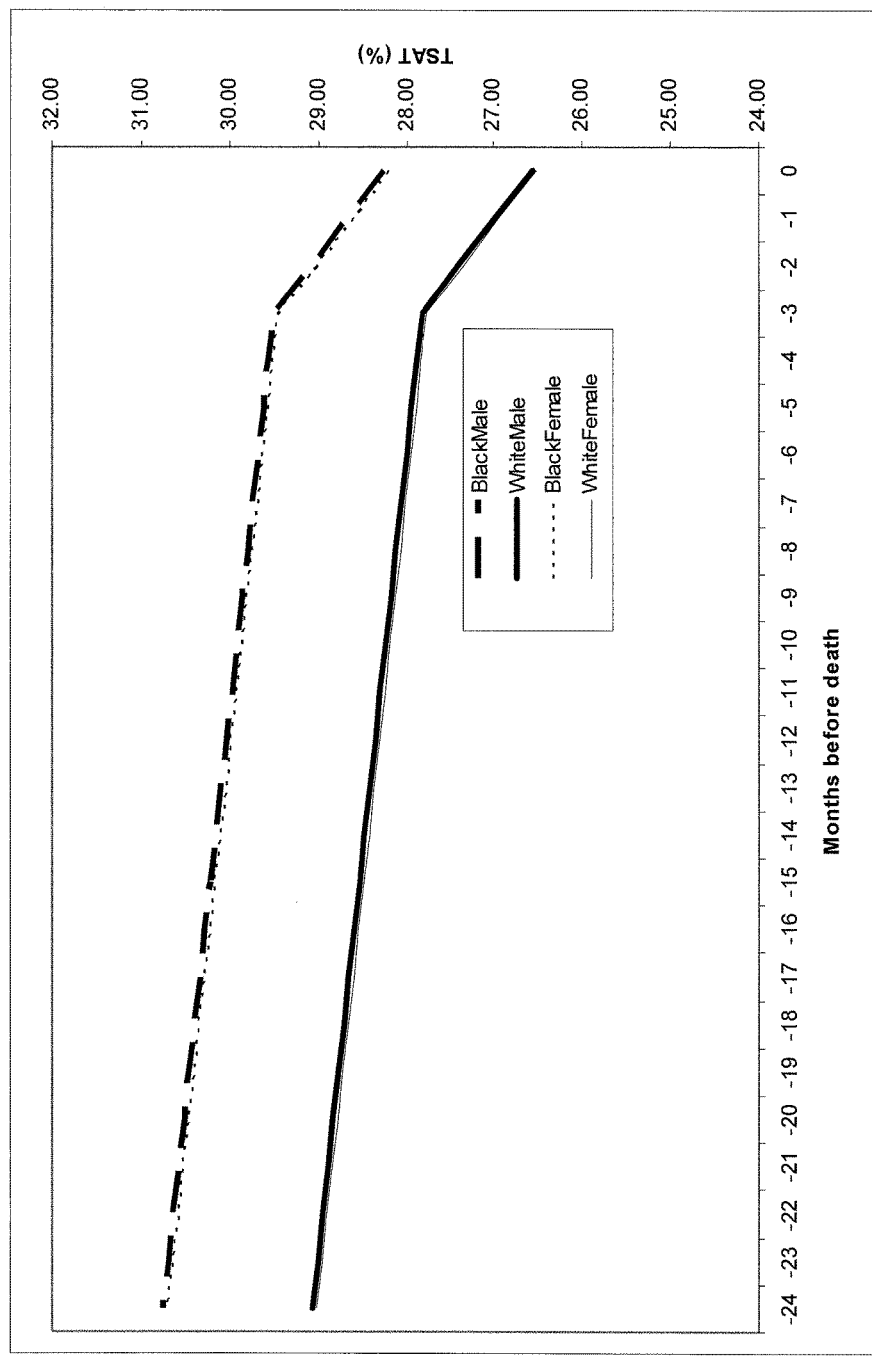
FIG. 14 is a graph of linear splines of transferrin saturation index of hemodialysis patients as a function of time before death; knot point at 3 months before death.

Turning now to FIG. 14, it was found that the transferrin saturation index (TSAT) of patients, typically measured in %, showed a change in the rate of decrease in the final 3 months of life, from a decrease of about 0.059% per month to a decrease of about 0.419% per month. Therefore, in this study, for transferrin saturation index, the rate of decrease increased by a factor of about 7 in the final 3 months of life. A low TSAT is seen with iron deficiency or inflammation.

Figure 15:
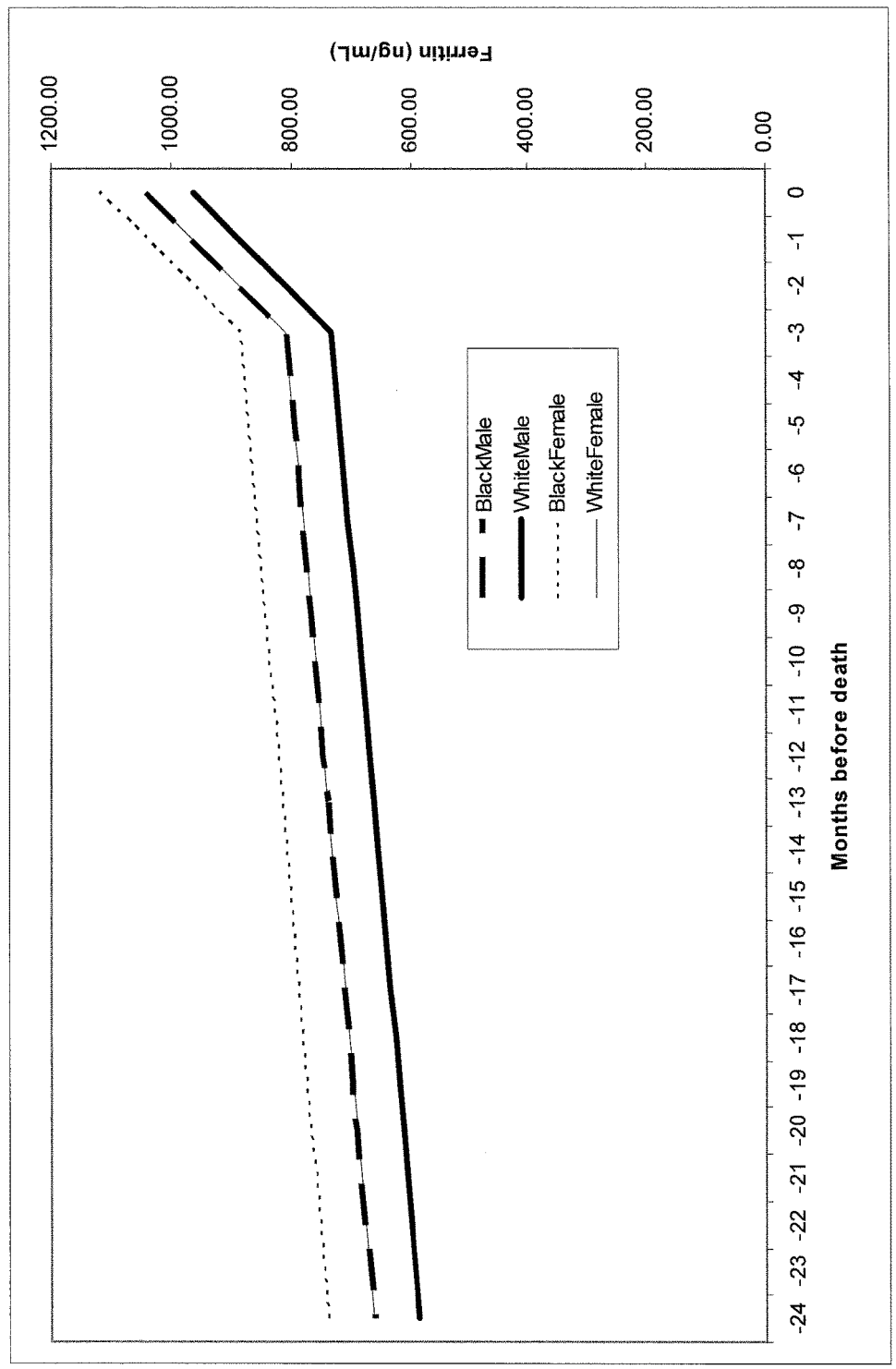
FIG. 15 is a graph of linear splines of serum ferritin concentration levels of hemodialysis patients as a function of time before death; knot point at 3 months before death.

Turning now to FIG. 15, it was found that the serum ferritin concentration levels of patients, typically measured in ng/mL, showed a change in the rate of increase in the final 3 months of life, from an increase of about 7.018 ng/mL/month to an increase of about 77.162 ng/mL/month. Therefore, in this study, for ferritin concentration level, the rate of increase increased by a factor of about 11 in the final 3 months of life. A high serum ferritin concentration level is indicative of inflammation.

Figure 16:
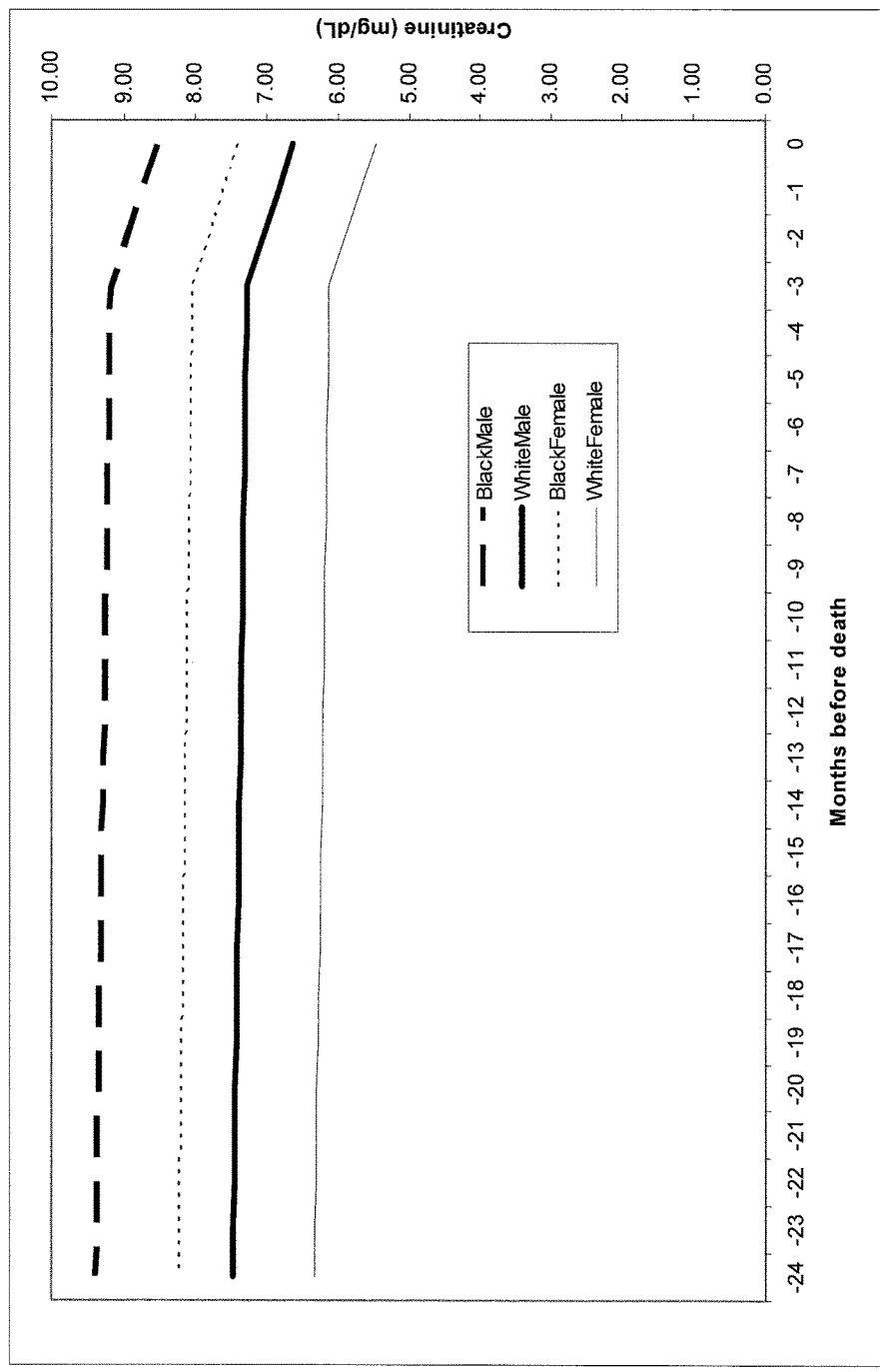
FIG. 16 is a graph of linear splines of serum creatinine concentration levels of hemodialysis patients as a function of time before death; knot point at 3 months before death.

Turning now to FIG. 16, it was found that the serum creatinine concentration levels of patients, typically measured in mg/dL, showed a change in the rate of decrease in the final 3 months of life, from a decrease of about 0.010 mg/dL/month to a decrease of about 0.215 mg/dL/month. Therefore, in this study, for serum creatinine concentration level, the rate of decrease increased by a factor of about 21 in the final 3 months of life. A decrease in serum creatinine concentration level is indicative of a loss of muscle mass.

Figure 17:
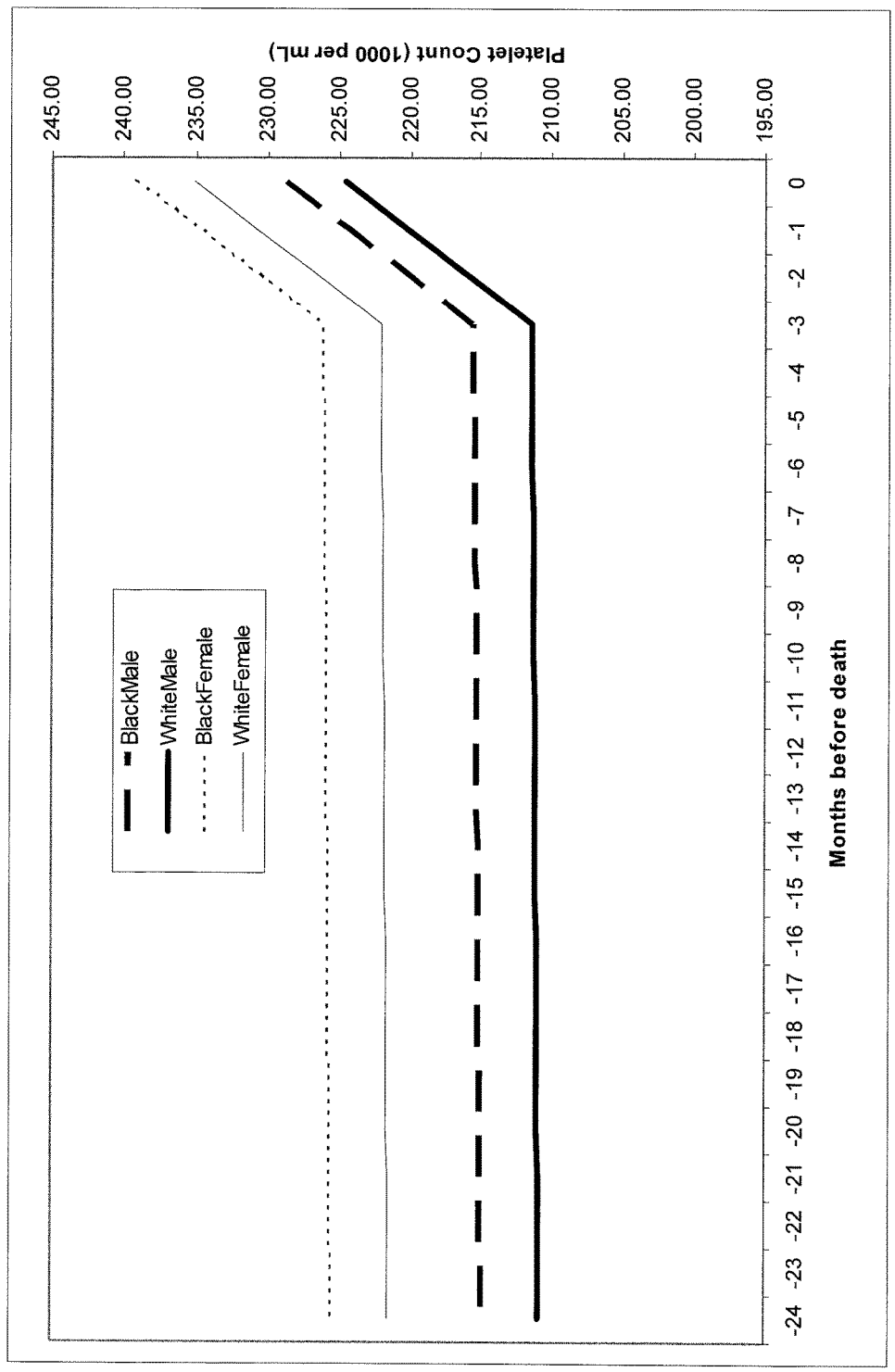
FIG. 17 is a graph of linear splines of platelet counts of hemodialysis patients as a function of time before death; knot point at 3 months before death.

Turning now to FIG. 17, it was found that the platelet count of patients, typically measured in 1000 per µL of blood, showed a change in the rate of increase in the final 3 months of life, from an increase of about 0.030 per month to an increase of about 4.361 per month. Therefore, in this study, for platelet count, the rate of increase increased by a factor of about 145 in the final 3 months of life. An increase in platelet count is seen in inflammation.

Figure 18:
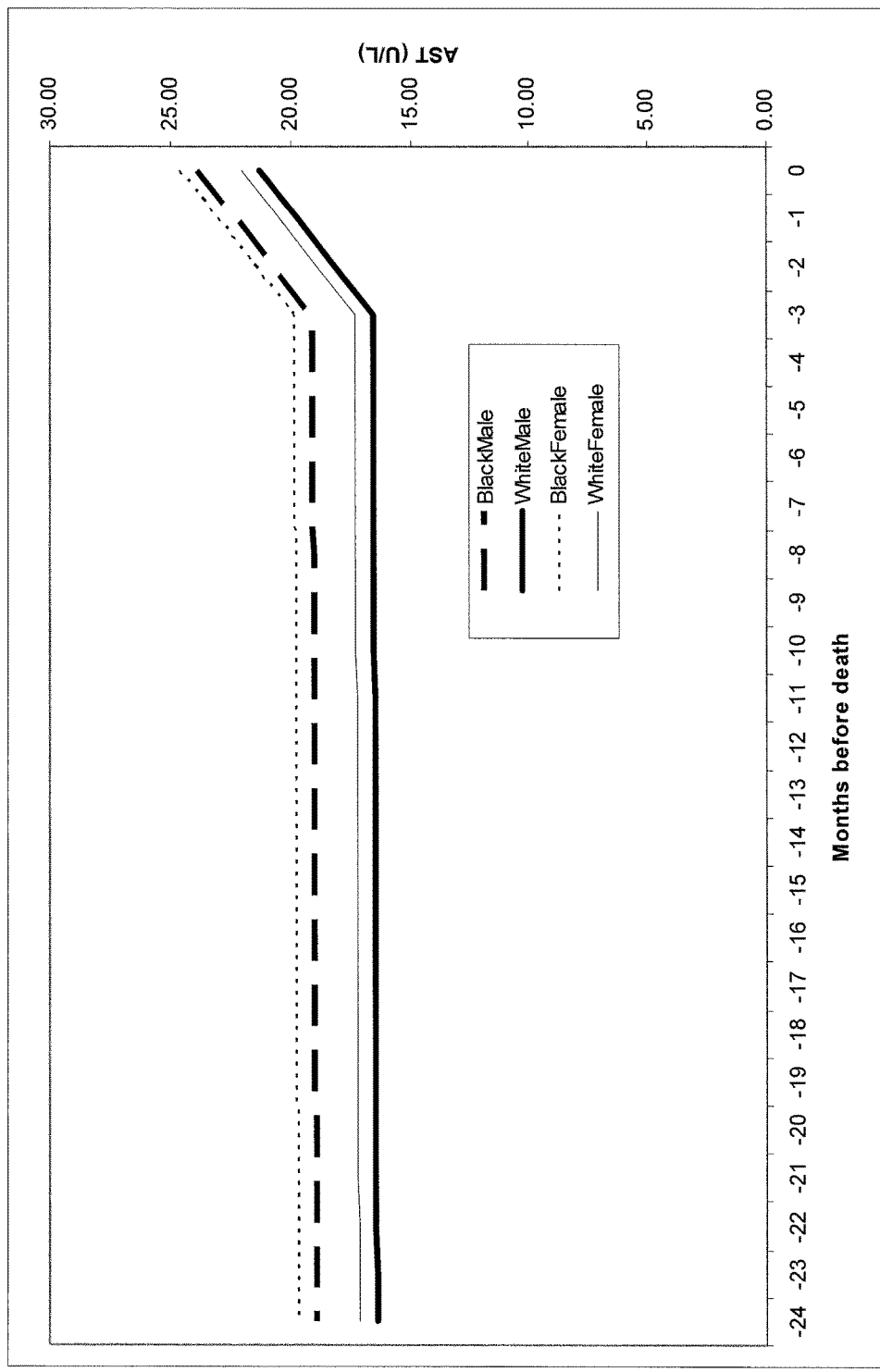
FIG. 18 is a graph of linear splines of Aspartat-Aminotransferase (AST) levels of hemodialysis patients as a function of time before death; knot point at 3 months before death.

Turning now to FIG. 18, it was found that the Aspartat-Aminotransferase (AST) level of patients, typically measured in U/L, showed a change in the rate of increase in the final 3 months of life, from an increase of about 0.007 per month to an increase of about 1.585 per month. Therefore, in this study, for Aspartat-Aminotransferase level, the rate of increase increased by a factor of about 226 in the final 3 months of life. An increase in Aspartat-Aminotransferase level is seen in liver and muscle disorders.

Figure 19:
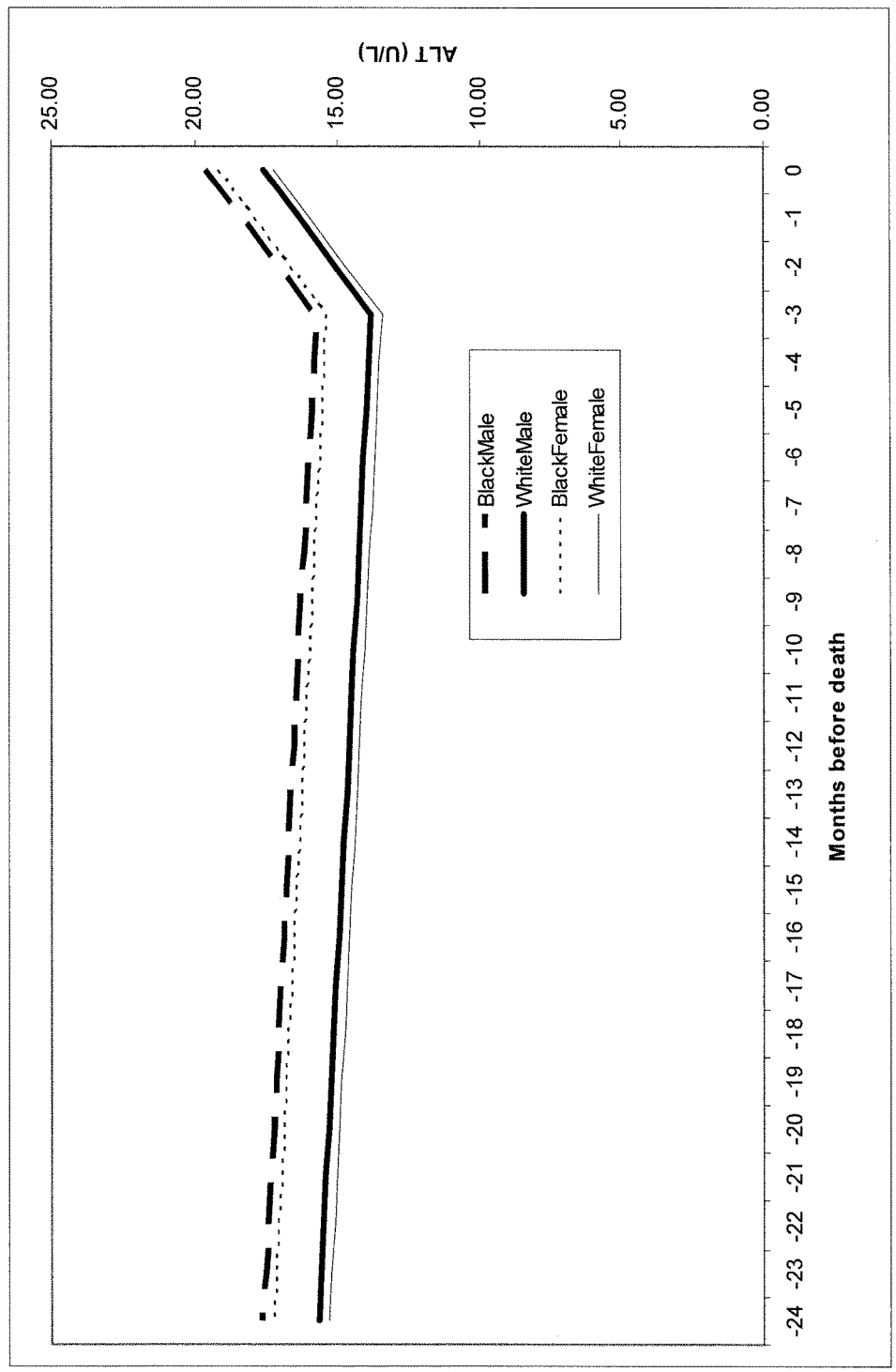
FIG. 19 is a graph of linear splines of Alanin-Aminotransferase (ALT) levels of hemodialysis patients as a function of time before death; knot point at 3 months before death.

Turning now to FIG. 19, it was found that the Alanin-Aminotransferase (ALT) level of patients, typically measured in U/L, showed a change in the rate of change in the final 3 months of life, from a decrease of about 0.088 per month to an increase of about 1.270 per month. Therefore, in this study, for Alanin-Aminotransferase level, the rate of change showed a change in character (from decrease to increase) in the rate of change in the final 3 months of life. An increase in Alanin-Aminotransferase level is seen in liver and muscle disorders.

There are a number of other clinical or biochemical parameters that can be used to identify a hemodialysis patient at increased risk of death. Generally, these parameters can be grouped into four domains, the cardiovascular, nutrition, inflammatory, and anthropometric domains. Examples in the cardiovascular domain include the diastolic and mean blood pressure, and the pulse pressure (systolic blood pressure minus diastolic blood pressure) and heart rate. Examples in the inflammatory domain include the IL-6 level, and the C-reactive protein level. Examples in the anthropometric domain include body mass index and body composition indices.

An "alert" level, notifying a physician that a patient is at increased risk of death, can be established by detecting a substantial change in the rate of decline or the rate of increase of at least one of the clinical and biochemical parameters discussed above, or any combinations of them. The substantial change that triggers a physician notification can a substantial change in the same direction, that is, a substantial increase in the rate of increase or a substantial decline in the rate of decline, or, alternatively, a substantial change in the opposite direction (e.g., a decrease in the serum potassium concentration level, or an increase in the Alanin-Aminotransferase level).

When a patient is "alert" flagged, certain diagnostic procedures can be triggered. These includes, but are not limited to: 1) the taking of a thorough history and physical examination with the specific aim to search for cardiovascular, inflammatory, and infectious conditions, 2) blood tests, including C-reactive protein (CRP), albumin, red and white cell blood counts, troponin, blood cultures, 3) echocardiogram, electrocardiogram, 4) chest x-ray, 5) imaging, in particular ultrasound, computer tomography and/or magnetic resonance imaging, 6) endoscopy, and 7) bacterial cultures and swabs.

Three broad categories of diagnoses can account for >80% of all diagnoses: cardiovascular disease (especially congestive heart failure (CHF) and coronary artery disease (CAD)), inflammation, and infection.

In cases of CHF and/or CAD, therapeutic interventions include but are not limited to: strict volume control, which includes avoidance of intradialytic administration of sodium and sodium loading via the dialysate, dietary salt intake below 6 g/day, increased dialysis frequency, drug therapy (angiotensin converting enzyme inhibitors (ACEI), angiotensin receptor blockers (ARB), beta blockers (BB)), lipid lowering drugs, replacement of deficient hormones, valve repair, and percutaneous transluminal coronary angioplasty.

In cases of inflammation without evidence of infection, therapeutic interventions include but are not limited to: removal of in-dwelling lines and catheters, therapy with anti-inflammatory drugs, broad spectrum antibiotic therapy, treatment of periodontal disease, and removal of rejected transplants and non-functioning vascular access.

In cases of infection, therapeutic interventions include but are not limited to: antibiotic therapy, mechanical and chemical debridement, and removal of in-dwelling lines and catheters.

In all "alert" flagged patients a comprehensive nutritional assessment is usually warranted. In cases of poor nutritional status, therapeutic interventions can include but are not limited to intradialytic parenteral nutrition and oral supplements.

All of the previously described diagnostic and therapeutic interventions on patients are more effective with earlier identification that the hemodialysis patient is at an increased risk of death, with 12 weeks or 3 months of lead time being sufficiently early for an effective intervention.

The relevant teachings of all patents, published applications and references cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying and treating a patient undergoing periodic hemodialysis treatments at increased risk for death, comprising:

a) determining at least one of the group of clinical or biochemical parameters consisting of serum bicarbonate concentration level, hemoglobin concentration level, Erythropoietin (EPO) resistance index, transferrin saturation index (TSAT), serum ferritin concentration level, serum creatinine concentration level, platelet count, and Aspartat-Aminotransferase level of the patient periodically while the patient is undergoing hemodialysis treatments;
   b) identifying the patient as having an increased risk for death if the patient has an increase in a rate of increase or decrease of the at least one clinical or biochemical parameter; and
   c) administering to the patient identified as having an increased risk for death a therapeutic intervention to decrease the patient's risk of death.

2. The method of claim 1, wherein identifying the patient as having an increased risk of death is accomplished at a time that allows for the therapeutic intervention to decrease the patient's risk of death.

3. The method of claim 2, wherein the patient is identified as having an increased risk of death at least 12 weeks prior to a predicted date of death.

4. The method of claim 1, wherein the increase in the rate of increase or decrease is by at least a factor of two.

5. A method of identifying and treating a patient undergoing periodic hemodialysis treatments at increased risk for death, comprising:

a) determining at least one of the group of clinical or biochemical parameters consisting of serum potassium concentration level, serum calcium concentration level, equilibrated fractional clearance of total body water by dialysis and residual kidney function (eKdrt/V), and Alanin-Aminotransferase level of the patient periodically while the patient is undergoing hemodialysis treatments;
   b) identifying the patient as having an increased risk for death if the patient has a change in character in the rate of change of the at least one clinical or biochemical parameter; and
   c) administering to the patient identified as having an increased risk for death a therapeutic intervention to decrease the patient's risk of death.

6. The method of claim 5, wherein the change in character is a change from a steady level to an increase or a decrease in the rate of change of the at least one clinical or biochemical parameter.

7. The method of claim 5, wherein the change in character is a change from a decrease to an increase, or an increase to a decrease, in the rate of change of the at least one clinical or biochemical parameter.

8. The method of claim 5, wherein identifying the patient as having an increased risk of death is accomplished at a time that allows for the therapeutic intervention to decrease the patient's risk of death.

9. The method of claim 8, wherein the patient is identified as having an increased risk of death at least 12 weeks prior to a predicted date of death.

* * * * *